United States Patent [19]
Muller et al.

[11] Patent Number: 5,973,110
[45] Date of Patent: *Oct. 26, 1999

[54] CYTOTOXIC T-LYMPHOCYTE ANTIGEN AS CYSTEINE PROTEASE INHIBITOR

[75] Inventors: Daniel Muller, Orange; Katherine Delaria, West Haven; Linda Wallace, East Haven, all of Conn.; Elise Brownell, Lafayette, Calif.

[73] Assignee: Bayer Corporation, Pittsburgh, Pa.

[ * ] Notice: This patent is subject to a terminal disclaimer.

[21] Appl. No.: 08/373,215

[22] PCT Filed: Jul. 15, 1993

[86] PCT No.: PCT/US93/06552

§ 371 Date: May 18, 1995

§ 102(e) Date: May 18, 1995

[87] PCT Pub. No.: WO94/02504

PCT Pub. Date: Feb. 3, 1994

Related U.S. Application Data

[63] Continuation-in-part of application No. 07/915,923, Jul. 17, 1992, abandoned.

[51] Int. Cl.$^6$ .............................. C07K 7/00; C07K 7/08; C07K 14/00
[52] U.S. Cl. ............................. 530/326; 530/300
[58] Field of Search ..................................... 530/350, 324, 530/300, 326; 514/12

[56] References Cited

U.S. PATENT DOCUMENTS 5,189,144  2/1993  Asada et al. ............................. 530/324

OTHER PUBLICATIONS

S. Gal and M. Gottesman "Isolation and sequence of a cDNA for human pro–(cathepsin L)" *Biochem. J.* 253(1): 303–306 (1988).

B.R. Tron et al., "Sequence and expression of the cDNA for MEP (major excreted protein), a transformation–regulated secreted cathepsin" *Biochem. J.* 246(3): 731–735 (1987).

L.J. Joseph et al., "Complete nucleotide and deduced amino acid sequences of human and murine preprocathepsin L" *J. Clin. Invest.* 81(5): 1621–1629 (1988).

F. Denizot et al., "Novel structures CTLA–2alpha and CTLA–2beta expressed in mouse activated T cells and mast cells and homologus to cysteine proteinase proregions" *Eur. J. Immunology* 19: 631–635 (1989).

*Primary Examiner*—George C. Elliott
*Assistant Examiner*—Sean McGarry
*Attorney, Agent, or Firm*—McDonnell Boehnen Hulbert & Berghoff

[57] ABSTRACT

Disclosed are molecules which inhibit the proteolytic activity of cysteine proteases such as Cathepsin H, Cathepsin L and papain, and methods for using molecules which have the biological properties of cytotoxic T-lymphocyte antigen for inhibiting cysteine proteases and inhibiting proteoglycan degradation.

7 Claims, 14 Drawing Sheets

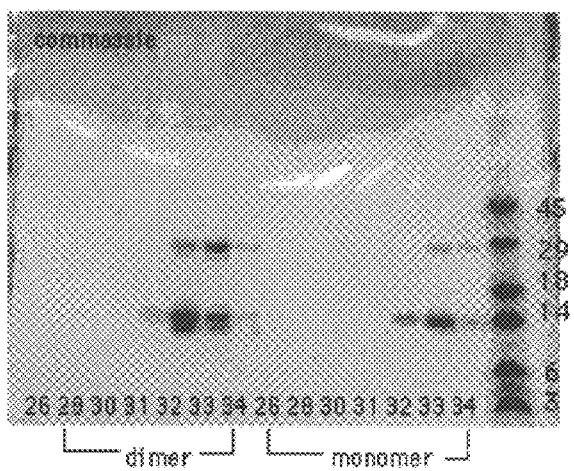 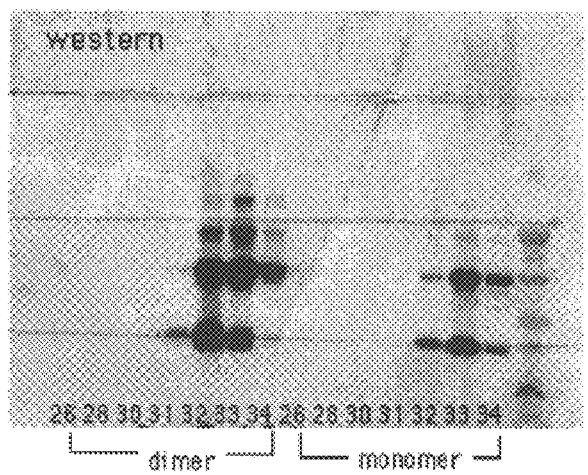
Figure 4 C　　　　　　　　　Figure 4 D

Figure 8 A) Cathepsin H
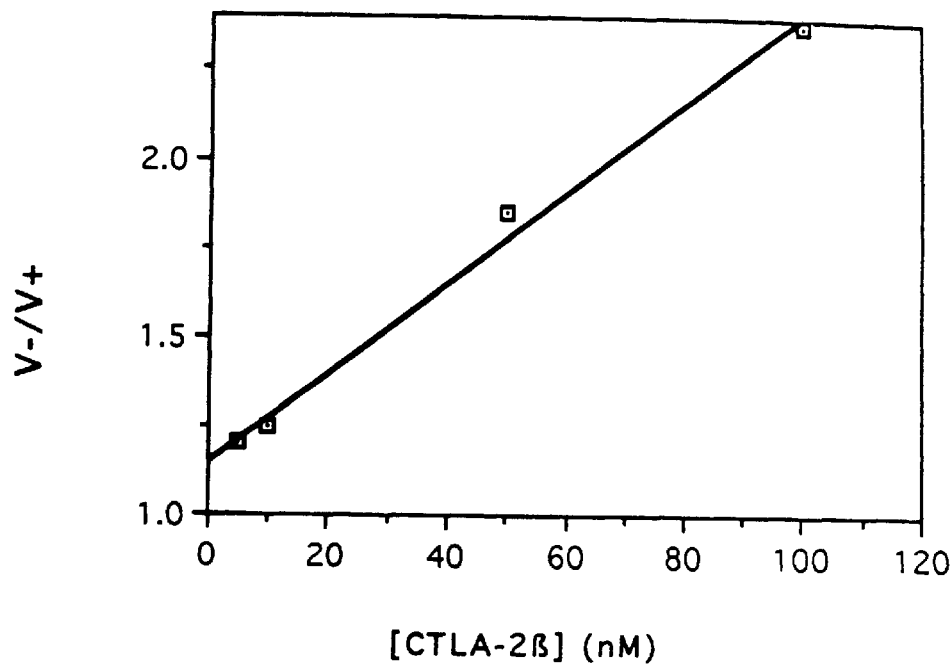
Figure 8 B) Papain
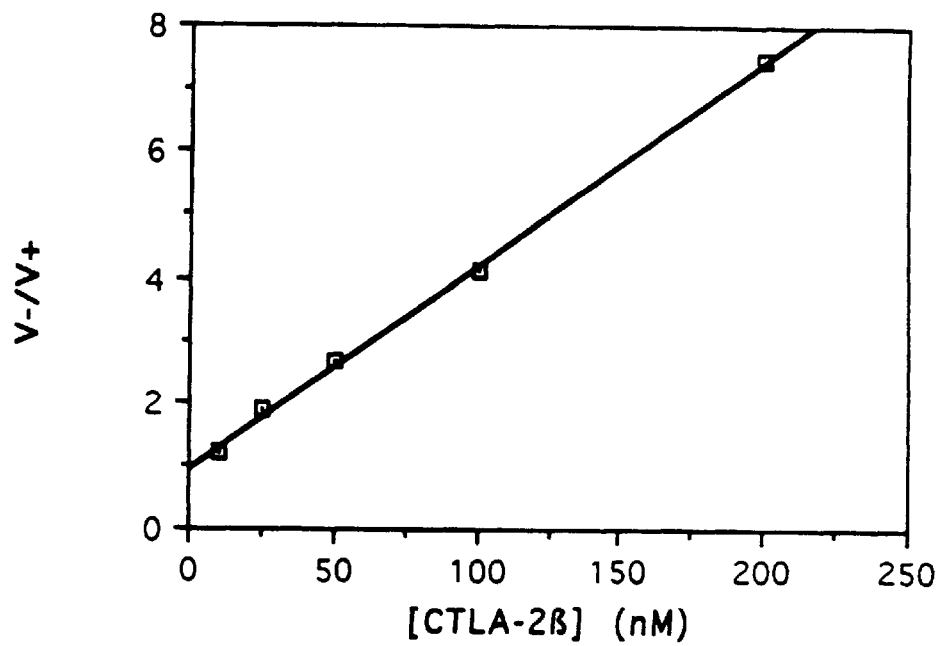

CYTOTOXIC T-LYMPHOCYTE ANTIGEN AS CYSTEINE PROTEASE INHIBITOR

This application is a continuation in part application of U.S. application Ser. No. 07/915,923, filed on Jul. 17, 1992, now abandoned, and a 371 of PCT/US93/06552, filed Jul. 15, 1993.

FIELD OF THE INVENTION

The present invention relates to methods for inhibiting the bio-activity of enzymes. More specifically, the invention comprises molecules having cytotoxic T-lymphocyte antigen properties, and methods of inhibiting the proteolytic activity of cysteine protease using such molecules.

DESCRIPTION OF THE RELATED ART

Cytotoxic T-Lymphocyte Antigen-2 (abbreviated CTLA-2) is a molecule expressed by activated T-cells and mast cells. Complementary DNA (cDNA) for two distinct but homologous forms of CTLA-2 are known, namely CTLA-2α and CTLA-2β (Denizot et al., 1989, Eur. J. Immunol., 19:631–635).

The present specification describes the identification of the gene encoding for peptides with CTLA-2 activity, and the expression, purification and characterization of such peptides having CTLA-2 activity. The identified gene for CTLA-2β codes for a protein consisting of 138 amino acids (15,900 g/mole) including a putative leader sequence. Removal of the hydrophobic N-terminus results in a protein of 110 amino acids (12,800 g/mole). There are a total of five cysteine residues in the molecule, two of which are in the putative leader sequence. Therefore, the mature protein should contain three cysteine residues indicating the formation of disulfide linked dimers.

The CTLA-2α gene codes for a protein which is 98% homologous (90% identical) to CTLA-2β at the protein level. CTLA-2α has a total of three cysteines in the full-length protein but only one in the mature form. Therefore, CTLA-2α also has the potential of forming a disulfide linked dimer.

The presently disclosed invention includes methods for inhibiting certain cysteine proteases with molecules having CTLA-2α and CTLA-2β activity. Members of the cysteine protease family all have cysteine in their active sites, and the family includes the enzyme papain found in the papaya plant, a developmentally regulated proteinase in the Dictyostelium slime mold, Chinese goosberry actinidin, and the mammalian lysosomal Cathepsins B, H, and L (Portnoy et al., 1986, J. Biol. Chem., 261:14697).

Cathepsins are proteolytic enzymes found in most mammalian cells and their functions include cellular autolysis and tissue degredation (Bohley et al., 1992, Experimentia, 48:151; Funabiki et al., 1990, Int. J. Biochem. 22:1303). Cathepsin L is a major lysosomal protease and is responsible for bulk turnover of intracellular protein. The cDNA sequence for CTLA-2β is known to be 40% homologous to the pro-region of mouse Cathepsin L (Denizot et al., id.), but there is no homology to the active protease sequence.

The present disclosure for the first time provides experimental evidence indicating that a protein homologous to the pro-region of a cysteine protease acts as an inhibitor of that cysteine protease. Specifically, the results hereinbelow show, inter alia, that purified CTLA-2β inhibits the proteolytic activity of the cysteine proteases papain, Cathepsin H and Cathepsin L.

There is a need in the art for inhibitors of cysteine proteases as these enzymes have been implicated in the formation of new foci of metastatic carcinoma (Aoyama et al., 1990, Biochem. 87:8296; Keren et al., 1988, Cancer Res., 48:1416; Sloane et al., 1984, Cancer Metastases Rev. 3:249; Stearns et al., 1990, Arch. Biochem. Biophys., 283:447). Inhibition of cysteine proteases is reported to be a good candidate for cancer therapy (Nakajima et al., 1991, Cancer Biology, 2:115).

In addition, there is further data implicating the role of cysteine proteases in the pathology of a number of diseases including: rheumatoid arthritis (Trabandt et al., 1990, Matrix, 10:349); glomerulonephritis (Baricos et al., 1991, Arch. Biochem. Biophys., 288:468); emphysema (Manson et al., 1986, Biochem. J., 233:925); osteoporosis (Delaisse et al., 1991, Biochem. J. 279:167); and Alzheimer's disease (Cole et al., 1989, Neurochemical Res., 14:933). Cysteine protease inhibitors should prove useful in the treatment of such disease states.

There have been a number of different synthetic organic compounds proposed as inhibitors of cysteine proteases and cathepsins, such as dipeptidyl aldehydes (Sasaki et al., 1990, J. Enzyme inhib., 3:13); C-terminal diazomethyl ketones (Wikstrom et al., 1989, Arch. Biochem. Biopys., 270:286); and trans-epoxysuccinyl-L-leucylamido-(4-guanido)butane, referred to as "E-64" (Baricos et al., Biochem. Biophys. Res. Comm., 155:1318).

However, such compounds have been found to be toxic as well as teratogenic (Fukushima et al., 1990, Toxicology and Applied Pharmacology, 185:1; Chen et al., 1989, Acta Paediatr. Jpn., 31:685; Tachikura, 1990, Acta Paeditr. Jpn. 32:495; Doherty et al., 1989, Exper. Cell Res., 185:506; Ivy et al., 1990, *Lipofuscin and Ceroid Pigments,* Plenum press, New York, pg. 31; Daston et al., 1991, Teratology, 43:253).

CTLA-2α and CTLA-2β are naturally occuring mammalian proteins and are not known to be either toxic or teratogenic Furthermore, physiologically, the CTLA-2 proteins act extracellularly in the inhibition of secreted cathepsins, and should not inhibit: cathepsins found intracellularlywithin lysosomes. Therefore, the normal functions of the cathespins inside cells should not be affected.

SUMMARY OF THE INVENTION

The present invention provides for the use of peptides as inhibitors of proteases and in particular specifically embody the peptides listed below.

The present invention provides for a polypeptide of the amino acid sequence:

Tyr-Ser-Leu-Asp-Glu-Glu-Arg-His-Arg-Arg-Leu-Met-Trp-Glu-Glu-Asn-Lys-Lys-Lys-Ile-Glu-Ala-His. (p117, SEQ ID NO. 5)

The present invention provides for a polypeptide of the amino acid sequence:

Ser-Leu-Asp-Asn-Glu-Trp-Lys-GLu-Trp-Lys-Thr-Thr-Phe-Ala-Lys-Ala-Tyr-Ser-Leu-Asp-Glu-Glu-Glu. (p118, SEQ ID NO. 6)

The present invention provides for a polypeptide of the amino acid sequence:

Glu-Asn-Lys-Lys-Lys-Ile-Glu-Ala-His-Asn-Ala-Asp-Tyr-Glu-Arg-Gly-Lys-Thr-Ser-Phe-(CYS). (p089, SEQ ID NO. 7)

The present invention provides for a polypeptide of the amino acid sequence:

Cys-Arg-Gly-Glu-Met-Ala-Pro-Asp-Leu-Pro-Glu-Tyr-Glu-Asp-Leu-Gly. (p092, SEQ ID NO. 8)

The present invention provides for a polypeptide of the amino acid sequence:

R R A V W E K N M K M I E L H N. (SEQ ID NO. 9)

The present invention provides for a polypeptide of the amino acid sequence:

R R A I W E K N M R M I Q L H N. (SEQ ID NO. 10)

The present invention provides for a polypeptide of the amino acid sequence:

R R L M W E E N K K K I E A H N. (SEQ ID NO. 11)

The present invention provides for a polypeptide of the amino acid sequence:

Thr-Leu-Thr-Phe-Asp-His-Ser-Leu-Glu-Ala-Gln-Trp-Thr-Lys-Trp-Lys-Ala-Met-His-Asn-Arg-Leu-Tyr-Gly-Met-Asn-Glu-Glu-Gly-Trp-Arg-Arg-Ala-Val-Trp-Glu-Lys-Asn-Met-Lys-Met-Ile-Glu-Leu-His-Asn-Gln-Glu-Tyr-Arg-Glu-Gly-Lys-His-Ser-Phe-Thr-Met-Ala-Met-Asn-Ala-Phe-Gly-Asp-Met-Thr-Ser-Glu-Glu-Phe-Arg-Gln-Val-Met-Asn-Gly-Phe-Gln-Asn-Arg-Lys-Pro-Arg-Lys-Gly-Lys-Val-Phe-Gln-Glu-Pro-Leu-Phe-Tyr Glu (SEQ ID NO. 12).

The present invention also provides for methods of inhibiting proteolytic activity of cysteine protease with the above listed peptides. In a preferred embodiment said cysteine protease is selected from the group consisting of Cathepsin H, Cathepsin L, Cathepsin B and papain. In a preferred embodiment the inhibiting peptide retains the activity of CTLA-2 and is substantially identical to the peptide described in SEQ ID NO. 4. In another preferred embodiment the inhibiting peptide is substantially identical to that described as p117 (SEQ ID NO. 5).

The present invention also provides for a method for inhibiting the degradation of proteoglycans with polypeptides. In a prefered embodiment the inhibiting polypeptide is selected from the group consisting of the polypeptides listed above. In a preferred embodiment the inhibiting peptide is substantially identical to that described as p117 (SEQ ID NO. 5).

The present invention also provides a method for inhibiting the degradation of proteoglycans in cartilage organ cultures by administering of an effective amount of an inhibiting peptide werein the inhibiting peptide is selected from the group listed above. In a preferred embodiment the inhibiting peptide is substantially identical to that described as p117 (SEQ ID NO. 5).

The present invention thus provides for compounds and methods useful for the treatment of diseases associated with degradation of proteoglycans, or the activity of cysteine proteases. Being protein based, the compounds of the present invention are advantageous in that there would be less toxicity when compared with the activity of chemical drugs that may inhibit some cysteine proteases. The present compounds are thus useful in themselves and as lead compounds for the development of derivatives with improved biological activity.

The invention comprises molecules with CTLA-2 activity, including bioactivites associated with CLTA-2α and CTLA-2β. Such molecules include isolated, purified recombinant proteins, synthetic analogs, oligopeptide fragments of the full lenath CTLA-2 proteins, and quarternary structural analogs such as dimeric or tetrameric forms of the CTLA-2 protein. In a preferred embodiment the protein is in a monomeric or dimeric form.

The invention also includes methods of inhibiting the enzyme activity of cysteine proteases using the above-stated molecules, such methods being adaptable by those skilled in the art for use as therapeutics for treatment of disease states whose causative agent is abnormal or excessive cysteine protease activity.

BRIEF DESCRIPTION OF THE DRAWINGS

FIG. 2(A) is a coomassie brilliant blue R-250 stain and FIG. 2(B) is a transfer to ProBlot for Western analysis.

FIG. 4(C) shows coomassie stain and FIG. 4(D) shows a western blot. Dimer fractions 26–34 are on the Left and monomer fractions 26–34 are on the Right for each gel.

FIGS. 5(A)–5(C) depict Circular Dichoism (CD) spectra of purified CTLA-2β. Each spectra is plotted as mean residual ellipticity vs. wavelength from 260 to 195 nm, with: FIG. 5(A) showing CTLA-2β monomer after Q-Sepharose chromatography, FIG. 5(B) showing CTLA-2β monomer after C4 reverse phase chromatography, FIG. 5(C) showing CTLA-2β dimer after C4 reverse phase chromatography.

FIGS. 8(A) and 8(B) show the determination of the I.C. 50 values for the inhibition of papain and Cathepsin H using the Dixon plot of the form V−/V+ vs. CTLA-2β concentration, with: 8(A) showing data for the inhibition of Cathepsin H by CTLA-2β, using H-Arg-AMC as substrate, and 8(B) showing data for the inhibition of Papain by CTLA-2β using Z-Phe-Arg-AMC as the substrate.

showing a Dixon plot derived from the data of 9(A). The various symbols plot different concentrations of peptide tested (in uM).

Figure 9:
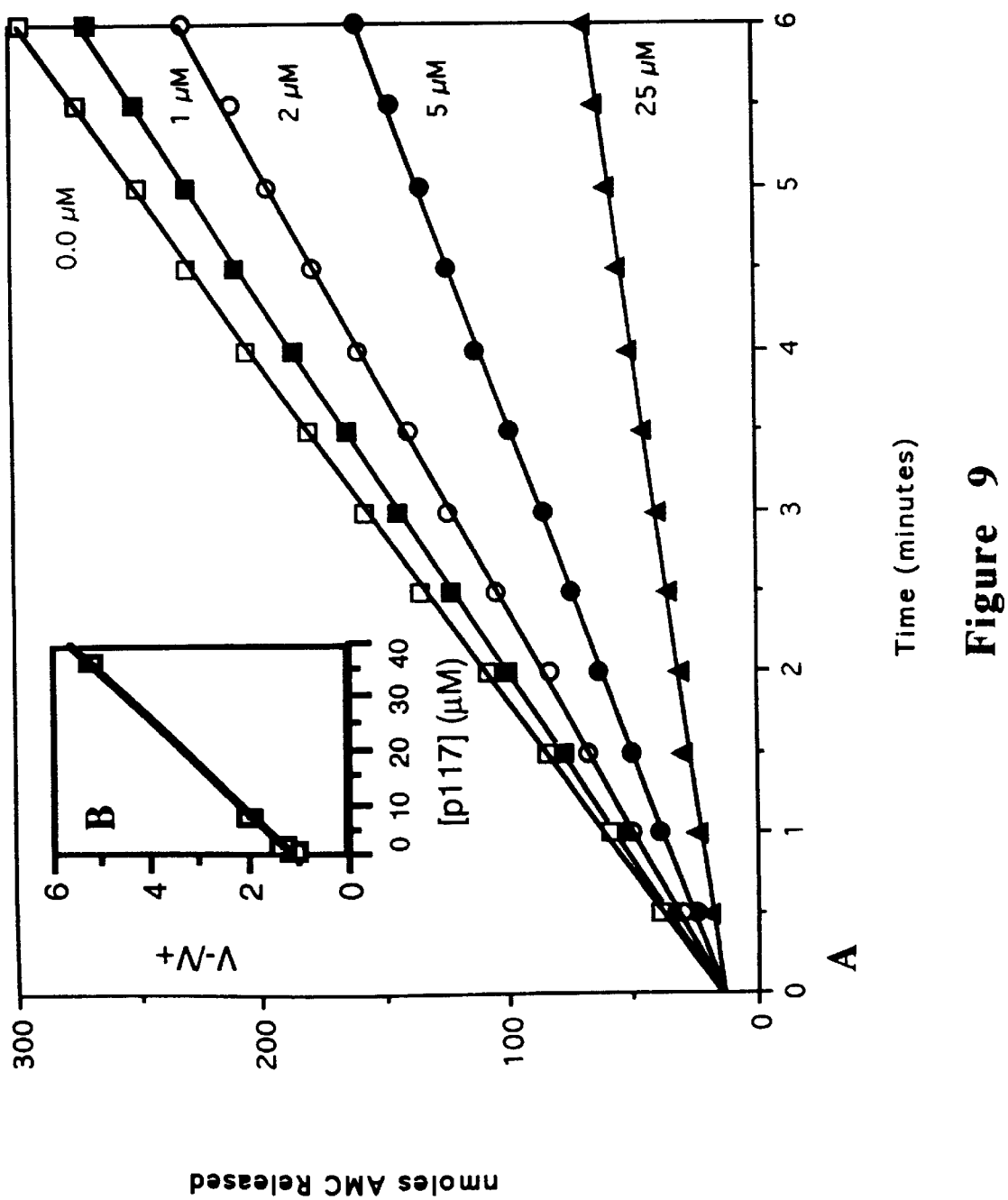
FIGS. 9(A) and 9(B) graphically depict inhibition of Cathepsin L using the synthetic p117 peptide [SEQ ID No. 5], the rate of AMC released was measured from linear regression of plots on nmoles AMC released over time. Dixon plots of the form V−/V+ vs. peptide concentration were made and the i.c. 50 determined, with: 9(A) showing the data for the inhibition of Cathepsin L by p117, and 9(B)
Figure 10:
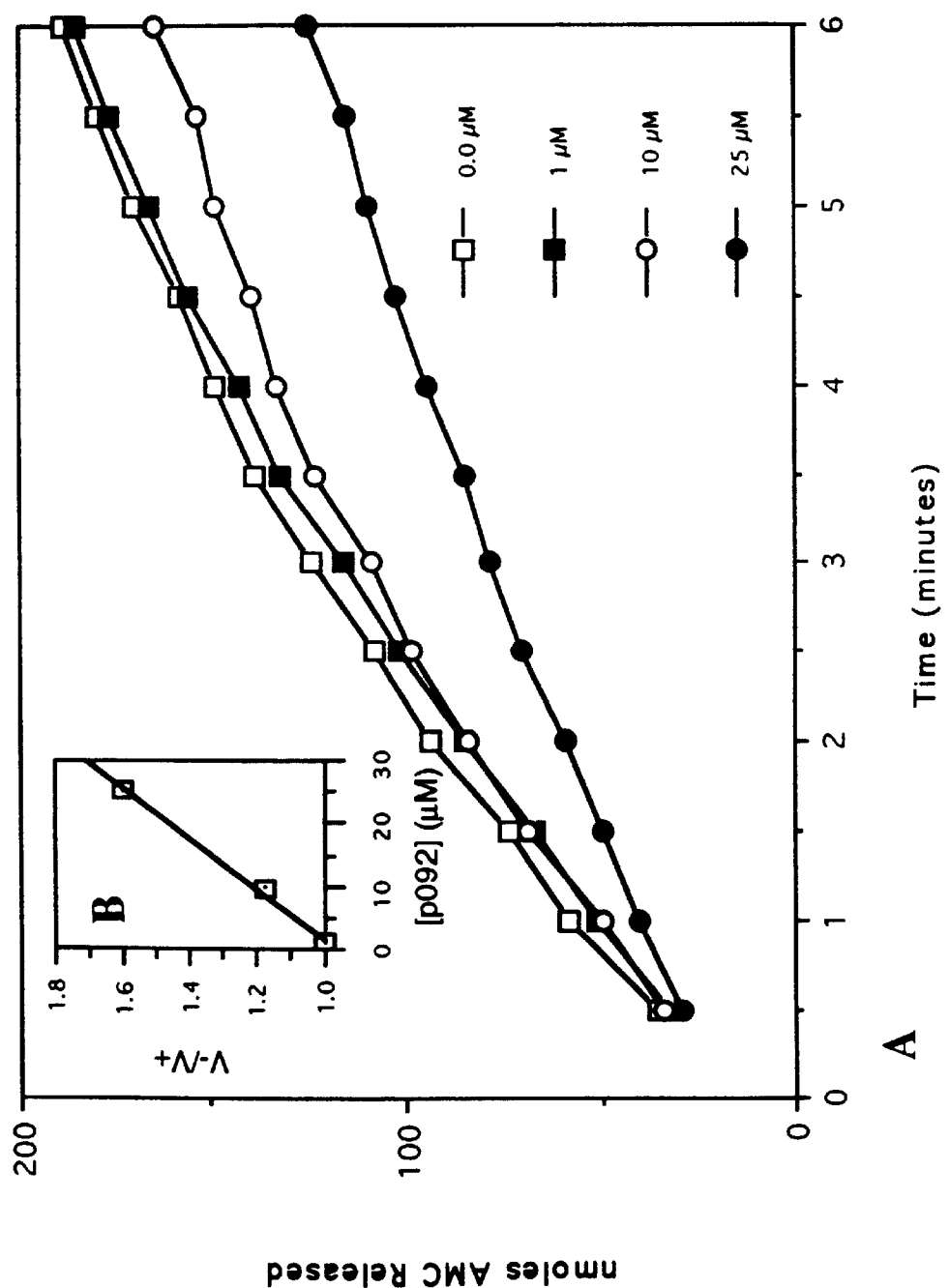

FIGS. 10(A) and 10(B) graphically depict inhibition of Cathepsin L using the p092 peptide [SEQ ID No. 8] as in FIG. 9, with: 10(A) showing the data for the inhibition of Cathepsin L by p092, and 10(B) showing a Dixon plot derived from the data of 10(A). The various symbols plot different concentrations of peptide tested (in uM) as labelled.

Figure 11:
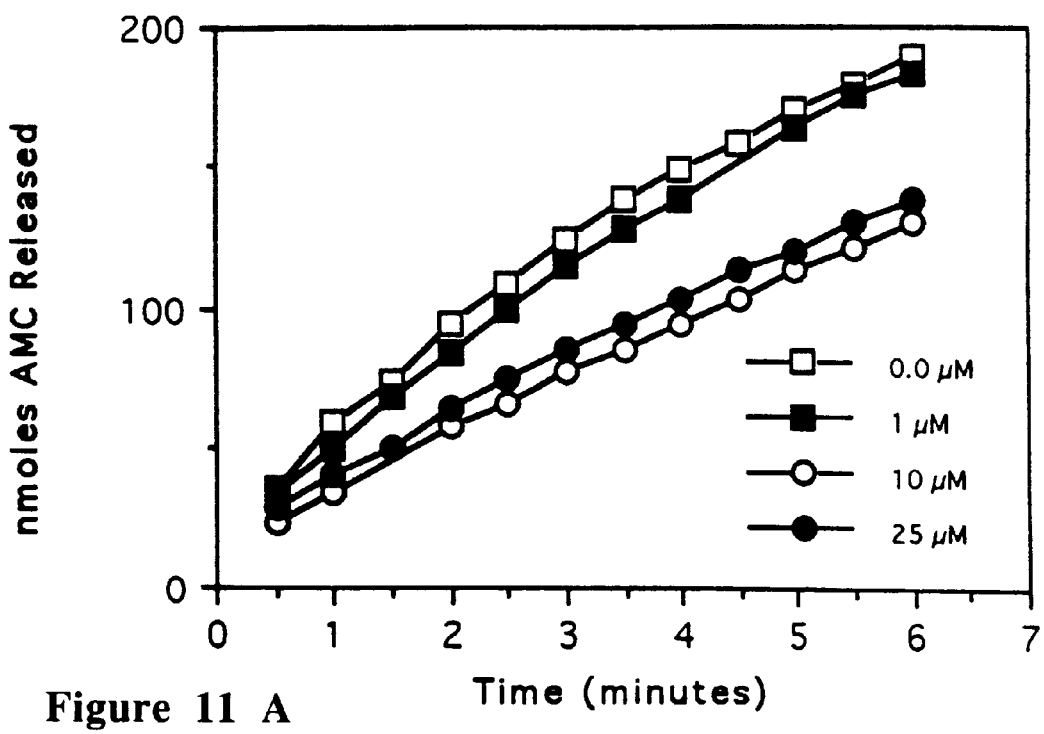
Figure 11:
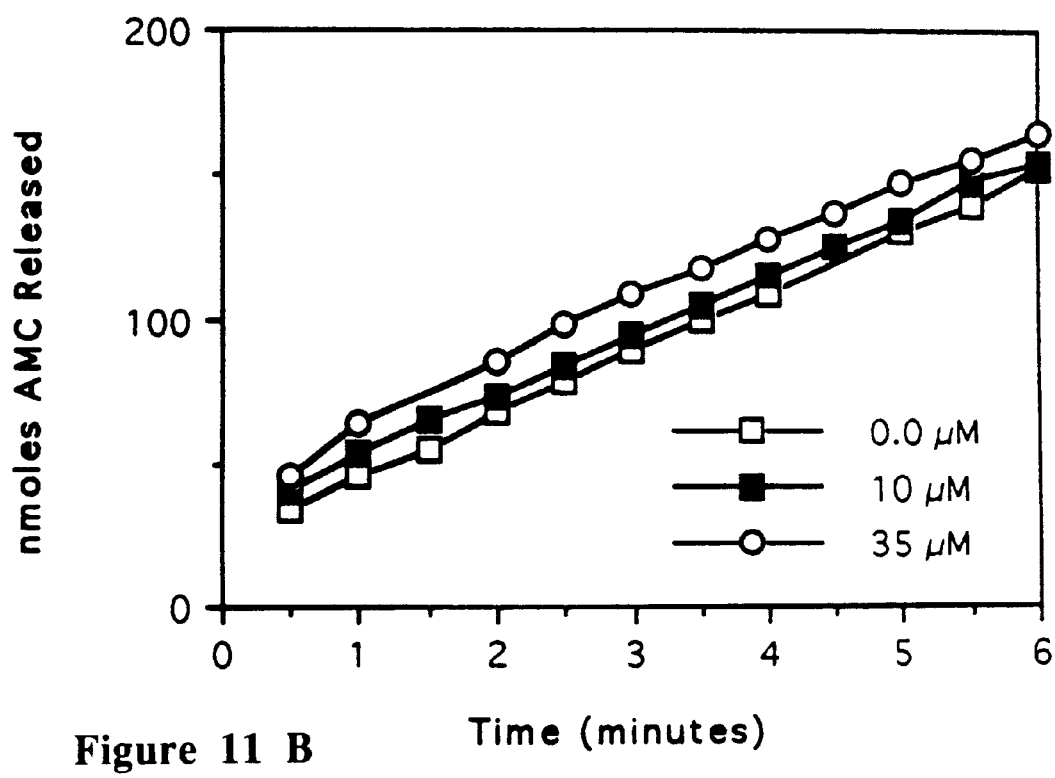

FIGS. 11(A) and 11(B) graphically depict inhibition of Cathepsin L using the p089 peptide, [SEQ ID No. 7] as in FIG. 9, with: 11(A) showing the data for the inhibition of Cathepsin L by p092, (open box 0.0 uM, closed box 1 uM, open circle 10 uM, closed circle 25 uM peptide) and: 11(B) showing a Dixon plot derived from the data of 11(A). (open box 0.0 uM, closed box 10 uM, and open circle 35 uM peptide). The rate of AMC released was measured from linear regression of plots on nmoles AMC released over time.

Figure 12:
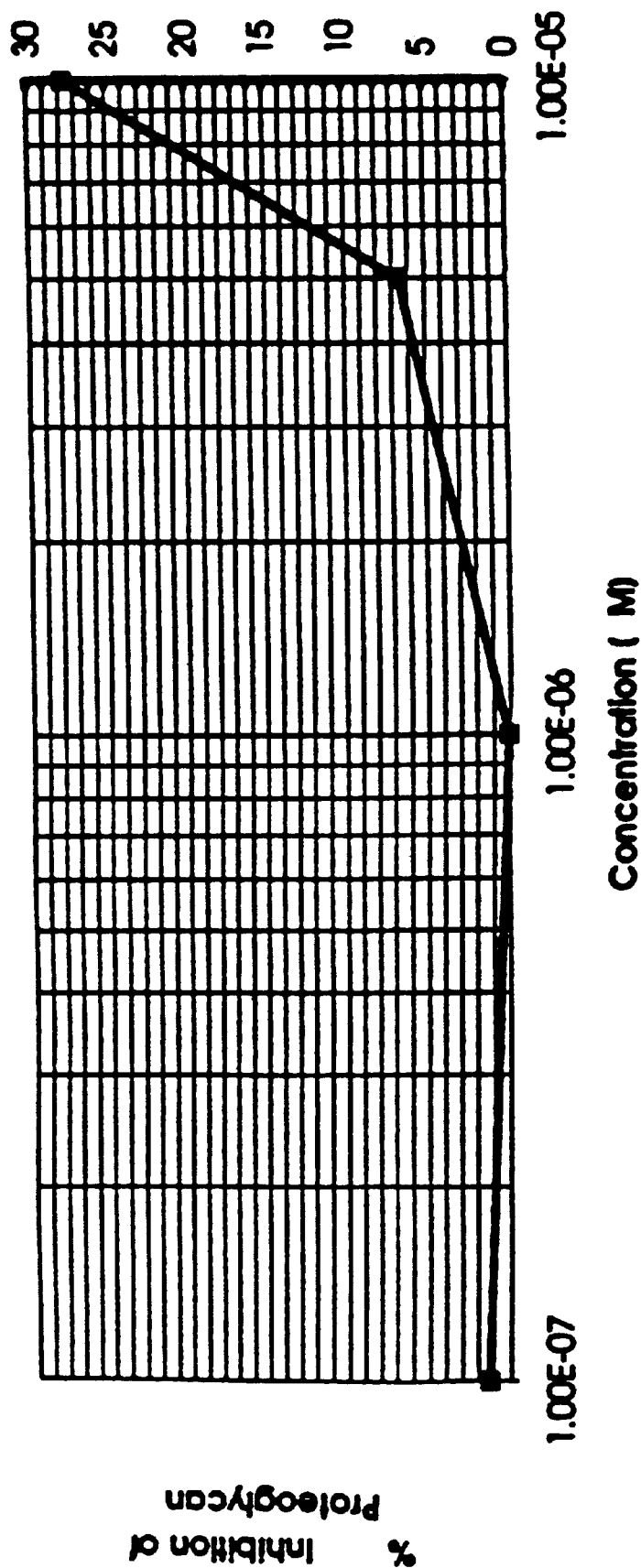

FIG. 12 is a graph showing inhibition by p117 peptide, of proteoglycan release from Cartilage Culture as tested by MOCA (Micro Organ Cartilage Culture Assay). The results are shown as % inhibition of proteoglycan release.

DETAILED DESCRIPTION OF THE INVENTION

The following describes the production of recombinant (murine) CTLA-2β in insect cells using a baculovirus overexpression system (Summers et al., 1987, *A Manual of Methods for Baculovirus Vectors and Insect Cell Culture Procedures,* Texas Ag. Exp. Sta. Bull. No. 1555); the purification of the overexpressed CTLA-2β using column chromatographic steps; and the demonstration that this recombinant protein, and fragments thereof, are inhibitors of the cysteine proteases such as human kidney cell cathepsins (Cathepsin H and Cathepsin L) and papain from the papaya plant.

EXAMPLE 1

Expression

The CTLA-2β gene was isolated from an eukaryotic expression cDNA library made from mRNA expressed by a murine T-cell hybridoma designated "AS-9" (Takashi Maki, New England Deaconess Hospital, Boston, Mass.).

This cDNA library was used in the expression screening protocol described in Aruffo et al., 1987, Proc. Natl. Acad. Sci. (USA), 84:3365, and Aruffo et al., 1987, EMBO J., 6:3313. This expression screening protocol yielded a molecular clone as shown below in SEQ ID NO. 1.

In order to express the recombinant protein in the baculovirus system, the putative leader sequence was removed. The SER residue, indicated by the underline, was changed to a MET residue to direct the synthesis of the recombinant protein in the baculovirus system. The protein sequence of the CTLA-2β predicted from the cloned gene is (SEQ ID NO. 1):

```
Leu Asp Asn Lys Val Leu Val Ser Ile Cys Glu Gln Lys Leu Gln His
1               5                   10                  15

Phe Ser Ala Val Phe Leu Leu Ile Leu Cys Leu Gly Met Met Ser Ala
            20                  25                  30

Ala Pro Ser Pro Asp Pro Ser Leu Asp Asn Glu Trp Lys Glu Trp Lys
        35                  40                  45

Thr Thr Phe Ala Lys Ala Tyr Ser Leu Asp Glu Glu Arg His Arg Arg
    50                  55                  60

Leu Met Trp Glu Glu Asn Lys Lys Lys Ile Glu Ala His Asn Ala Asp
65                  70                  75                  80

Tyr Glu Arg Gly Lys Thr Ser Phe Tyr Met Gly Leu Asn Gln Phe Ser
                85                  90                  95

Asp Leu Thr Pro Glu Glu Phe Arg Thr Asn Cys Cys Gly Ser Ser Met
            100                 105                 110

Cys Arg Gly Glu Met Ala Pro Asp Leu Pro Glu Tyr Glu Asp Leu Gly
            115                 120                 125

Lys Asn Ser Tyr Leu Thr Pro Gly Arg Ala Gln Pro Glu
            130                 135                 140
```

The following synthetic oligonucleotide fragments were used as primers to generate a subfragment of CTLA-2β via polymerase chain reaction amplification:

5'Primer: (SEQ ID NO. 2)
GGGGGATCCA TGGCTGCTCC ATCC

3'Primer: (SEQ ID NO. 3)
TGTGGACCTT CCCGAGTCGG TCTCATTCGA TCGCCTAGGG GG

The generated subfragment was digested with NcoI and BamHI, and the truncated fragment was subsequently ligated into a PBL 1392 vector (Invitrogen, San Diego, Calif.) for high-level expression in the baculovirus/insect cell system (Invitrogen, CA.).

This construct contained the coding sequences for the mature form of CTLA-2β protein (i.e. without the putative leader sequence and with an additional methionine (MET) residue added at the proposed start of the mature protein, and had the following amino acid sequence: (SEQ ID NO. 4)

```
Met Ala Ala Pro Ser Pro Asp Pro Ser Leu Asp Asn Glu Trp Lys Glu
1               5               10                  15

Trp Lys Thr Thr Phe Ala Lys Ala Tyr Ser Leu Asp Glu Glu Arg His
            20              25                  30

Arg Arg Leu Met Trp Glu Glu Asn Lys Lys Lys Ile Glu Ala His Asn
            35              40              45

Ala Asp Tyr Glu Arg Gly Lys Thr Ser Phe Tyr Met Gly Leu Asn Gln
        50              55              60

Phe Ser Asp Leu Thr Pro Glu Glu Phe Arg Thr Asn Cys Cys Glu Ser
65              70                  75                      80

Ser Met Cys Arg Gly Glu Met Ala Pro Asp Leu Pro Glu Tyr Glu Asp
                85              90                  95

Leu Gly Lys Asn Ser Tyr Leu Thr Pro Gly Arg Ala Gln Pro Glu
            100             105             110
```

An alternate method for constructing the clone would be to use the above-mentioned oligonucleotide primers to generate the same CTLA-2β fragment directly from cDNA made from a suitable murine T-cell line such as KB5C20.

In order to optimize the growth of the SF9 cells and the expression of the recombinant CTLA-2β, a number of different multiplicity of infections (hereinafter "M.O.I.") and harvest times were tried. An M.O.I. of 1 and 10 were used, and for both M.O.I.'s a sample was analyzed for CTLA-2β expression at 48, 72, and 96 hours after infection. According to Western analysis of the supernatants and cell pellets, the best expression of secreted CTLA-2β was obtained at a M.O.I. of 10 with a 96 hour harvest time.

EXAMPLE 2

Purification of CTLA-2β

(i) Crude Supernatant: Baculovirus cell culture supernatant was supplemented with 1 mM PMSF, 5 mM each of benzamidine and EDTA, 5 μg/ml each of chymostatin, antipain, E-64, and aprotinin, 2 μg/ml leupeptin, and 1 μg/ml pepstatin. The solution was adjusted to pH 7.5 and clarified by centrifugation for 30 min. at 10K rpm. Material was stored at −20° C. until needed.

(ii) Superdex-75 Gel-Filtration Chromatography: All further purification operations were performed in a cold room at 2° C. A Pharmacia superdex-75HR 16/60 FPLC column was equilibrated in 50 mM Tris-HCl (pH 8.0) and 150 mM NaCl (Buffer A) and run at a flow rate of 1.5 ml/min. The Pharmacia FPLC system was set up to inject and run automatically. A volume of 4 ml of crude supernatant was applied and the column eluted isocratically in a total volume of 135 ml of equilibration buffer. Fractions (2.25 ml) were collected and analyzed by duplicate SDS-PAGE; which were either stained for total protein or analyzed for CTLA-2β through a Western blot (see Protein Analysis below). The fractions that contained CTLA-2β were pooled.

(iii) Q-Sepharose Anion-Exchange Chromatography: A Pharmacia 10/10 C-column containing 10 ml of Q-Sepharose was equilibrated in Buffer B (50 mM Tris-HCl pH 8.0, 25 mM NaCl) at a flow rate of 1.0 ml/min. The CTLA-2β pool from step (ii) was dialyzed against Buffer B using 6,000–8,000 molecular weight cut-off membrane (Spectrum), and loaded onto the Q-sepharose column. The column was then washed with three column volumes of Buffer B, and CTLA-2β was eluted subsequently in a 40 ml linear gradient of 0.5M NaCl in Buffer B at a flow rate of 0.75 ml/min. Fractions (1 ml) were collected and analyzed as in (ii). Fractions containing CTLA-2β were pooled and stored at 40C.

(iv) Reverse-phase Chromatography: reverse-phase chromatography was performed on a Beckman System Gold HPLC using a C4 column (Vydac, 25×1.0 cm). 2.5 ml (1.0 mg) of CTLA-2β from step (iii) was injected onto the C4 column previously equilibrated in 100 mM sodium acetate pH 6.5 at a flow rate of 2 ml/min. Material was eluted with a linear gradient of 5% to 80% acetonitrile over 45 min. Fractions (2 ml) were collected and analyzed as above.

EXAMPLE 3

Protein Characterization (i) Protein Determination: Protein concentrations were determined either by the Pierce dye binding assay using BSA as a standard, or by the absorbance at 280 nm using an extinction coefficient of $2.7 \times 10^4$ L/mol/cm (calculated by using the amino acid composition data to quantify the amount of protein)

(ii) SDS-PAGE: Protein samples were analyzed by SDS-PAGE on 10–20% tricine buffered acrylamide gels (Novex) under non-reducing conditions. Protein was detected with Coomassie Brilliant Blue R-250. Western blots were developed with affinity purified anti-peptide antibodies which were made to either the middle of the protein, (amino acids 69–88 of the mature sequence), or the C-terminal region (113–128). Alkaline-Phosphatase conjugated goat anti-Rabbit antibody was used as the secondary antibody, and the blot was developed according to standard protocols.

(iii) Secondary Structure: The secondary structure of CTLA-2β was determined using circular dichroism (CD). CTLA-2β from steps (iii) and (iv) of Example 2 (in PBS buffer) were analyzed using an AVIV associates circular dichroism spectrophotometer model 62DS. The spectra were corrected for the absorbance of the buffer.

(iv) Molecular Weight: The molecular weights of the monomeric or diimeric forms of CTLA-2β were determined by mass spectrometry. CTLA-2β from step (iv) of Example 2 was analyzed using a Finigan LASERMAT Laser-Desorbtion Time-of-Flight Mass Spectrophotometer.

EXAMPLE 4

Cysteine Protease Inhibition (i) Cathepsin L Assay: The capacity of CTLA-2β to inhibit the activity of the proteolytic enzyme Cathepsin L was measured. A fluorescence based assay was set up according to Barrett and Kirschke (Barrett et al., 1981, Meth. in Enz., 80:535).

The enzyme sample was diluted with 750 μl of assay buffer (340 mM sodium acetate—60 mM acetic acid—4 mM disodium EDTA, pH 5.5 and 8 mM DTT added fresh) and various concentrations of CTLA-2β (a final concentration of 5–50 nM), was added. After an incubation period of 6 minutes at room temperature, 1500 μl of 0.1% Brij 35 was added. The substrate Z-Phe-Arg-AMC (AMC is aminomethyl-coumarin) was added at a final concentration of either 2.5 μM or 5.0 μM.

The fluorescence of the free aminomethyl-coumarin was measured in an SLM 4800s fluorimeter by excitation at 370 nm and emission at 432 nm over a six minute time period. Fluorescence was plotted vs. concentration of CTLA-2β at the two substrate concentrations specified. In order to calculate the velocities, a linear least squares analysis was performed over the initial linear part of the data. The fluorescence of the reaction mixture was measured both with and without CTLA-2β present in order to determine the velocity with (V+) and without (V−) inhibitor.

The i.c. 50 values were determined from Dixon plots of the form V−/V+ vs. I. In order to calculate the Ki value for the interaction of CTLA-2β with Cathepsin L, 1/V was plotted vs. the concentration of CTLA-2β. The Ki value is equal to the negative of the X-axis intercept that gives the same velocity at the different substrate concentrations if there is competitive inhibition (Dixon et al., 1979, Enzymes, 3rd Ed., Academic Press, New York, page, 365).

(ii) Cathepsin H Assay: Cathepsin H was diluted in 750 μl of assay buffer (200 mM $KH_2PO_4$—200 mM $Na_2HPO_4$—4 mM disodium EDTA pH 6.8 and 40 mM Cysteine added fresh). CTLA-2β was added at a final concentration range of 5–200 nM, and reaction incubated as for Cathepsin L. The mixture was diluted with Brij 35 as in above, and the substrate H-Arg-AMC added at a final concentration of 5 μM. The fluorescence was measured as above, and the i.c. 50 determined.

(iii) Papain assay: The assay conditions used were identical to that of Cathepsin L with the exceptions that the final concentration of enzyme used was 33.3 ng/ml, the final concentration of CTLA-2β was 5–100 nM, and that the assay buffer was 88 nM $KH_2PO_4$—12 MM $Na_2HPO_4$—1.33 mM disodium EDTA 2.7 mM Cysteine added fresh. The fluorescence was measured and the i.c. 50 was determined.

RESULTS

A) Baculovirus Expression.

After performing the time course and multiplicity of infection experiments, the expression level of CTLA-2β was approximately 50 mg/L of conditioned media. Most of the expressed CTLA-2β was found in the cell culture supernatant and not inside the cells (data not shown). This observation is interesting because the construct used for the expression did not have the putative leader sequence attached and has an additional methionine residue at the N-terminus to direct the synthesis. The majority of the expressed CTLA-2β was monomeric, but some dimer form was observed.

B) Protein Purification.

Purification of the monomeric and dimeric forms of CTLA-2β was accomplished by a two-step protocol and yielded 2.5 mg of monomeric CTLA-2β per 168 ml culture (See Table 1, below).

TABLE I

PURIFICATION OF CTLA-2β MONOMER

| STEP | VOLUME (ml) | OD280/ml | TOTAL OD 280 | mg/ml | TOTAL mg |
|---|---|---|---|---|---|
| CELL CULTURE | | | | | |
| SUPERNATANT | 168.0 | 12.84 | 2157.1 | 2.97[a] | 498.5 |
| SUPERDEX 75 | 410.0 | 0.057 | 23.37 | 0.023[a] | 9.43 |
| Q-SEPHAROSE | 6.0 | 0.87 | 5.23 | 0.424[b] | 2.54 |

Purification of CTLA-2β from a 168.0 ml Baculovirus cell-culture supernatant.
[a]Concentration determined by Pierce assay.
[b]Concentration determined using an extinction coefficient of $2.67 \times 10^4$ L/mol/cm.

Figure 1:
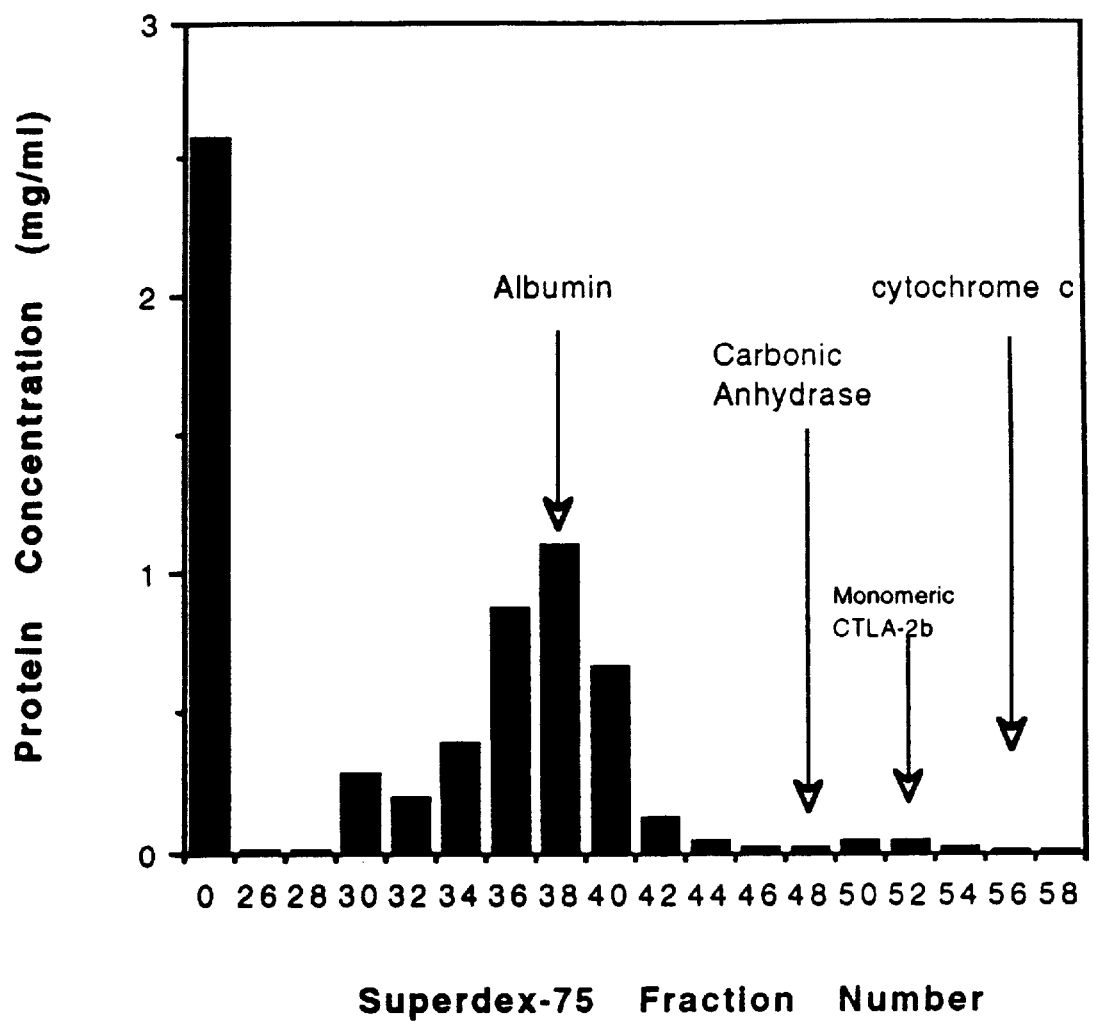
FIG. 1 is an elution profile for crude baculovirus supernatant chromatographed on Superdex-75. Protein concentration is plotted vs. fraction number. The position of protein standards is shown.
Figure 2:
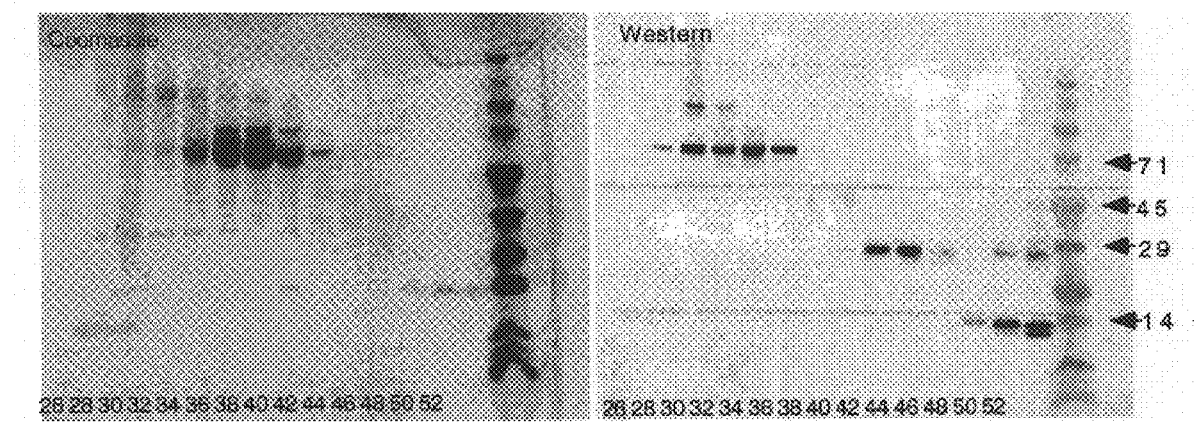
FIGS. 2(A) and 2(B) show purification of CTLA-2β by Superdex 75 gel filtration chromatography monitored by SDS-PAGE analysis of Superdex-75 purification fractions.

The original cell-culture supernatant was applied to a Superdex-75 Gel-Filtration column with most contaminants being removed in this step (see FIGS. 1 and 2). Several species that differed in their molecular weight were identified by western analysis (FIG. 2). Fractions 26–34 had a 75Kd molecular weight species which was visible only under non-reducing conditions. This 75Kd species disappeared if the sample was analyzed on a reducing SDS-PAGE. The exact nature of this species is unknown but it may represent cross-reactivity of the antibodies. Fractions 40–46 contained a band on the western blot of 27,000 g/mole; corresponding to a dimeric form of CTLA-2β. However, according to the elution profile of protein standards, the molecular weight of a protein eluting in this position should be approximately 45,000 g/mole, corresponding to a tetramer of CTLA-2β. Therefore, the covalently linked dimeric form of CTLA-2β probably forms a tetramer under non-denaturing conditions. Fractions 48–52 contained a band on the western blot of 13,000 g/mole, corresponding to monomeric CTLA-2β. However, this material eluted off of the gel filtration column at approximately 26,000 g/mole. This would be the correct molecular weight for a dimer. Therefore, it appears as if CTLA-2β can associate to form non-covalently linked dimers and that the dimers can associate to form a tetramer.

Figure 3:
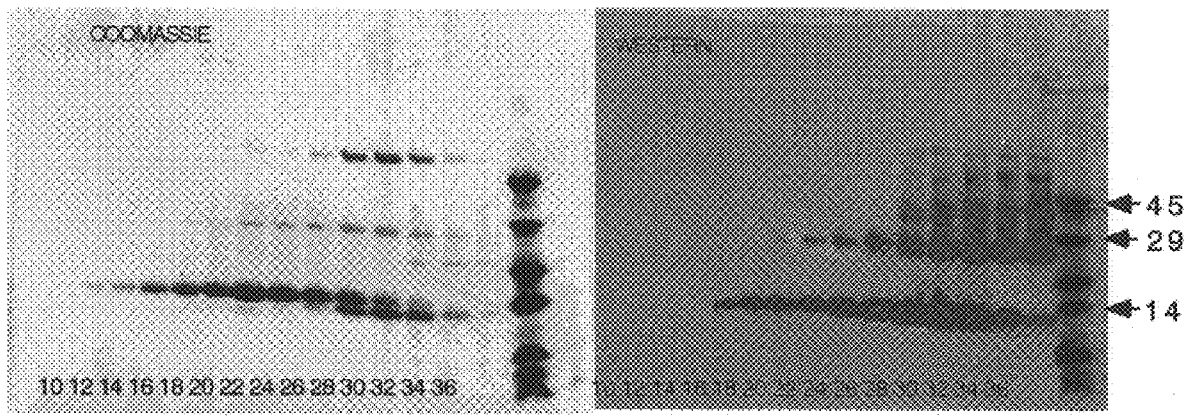
FIGS. 3(A) and 3(B) show SDS-PAGE analysis of Q-sepharose anion-exchange purification fractions of CTLA-2β as monitored by SDS-Page. (10%–20% tricine under non-reducing conditions.) Gel was stained for total protein with coomassie brilliant blue R-250 as shown in 3(A) or transferred to ProBlot for western analysis as shown in 3(B).
Figure 4:
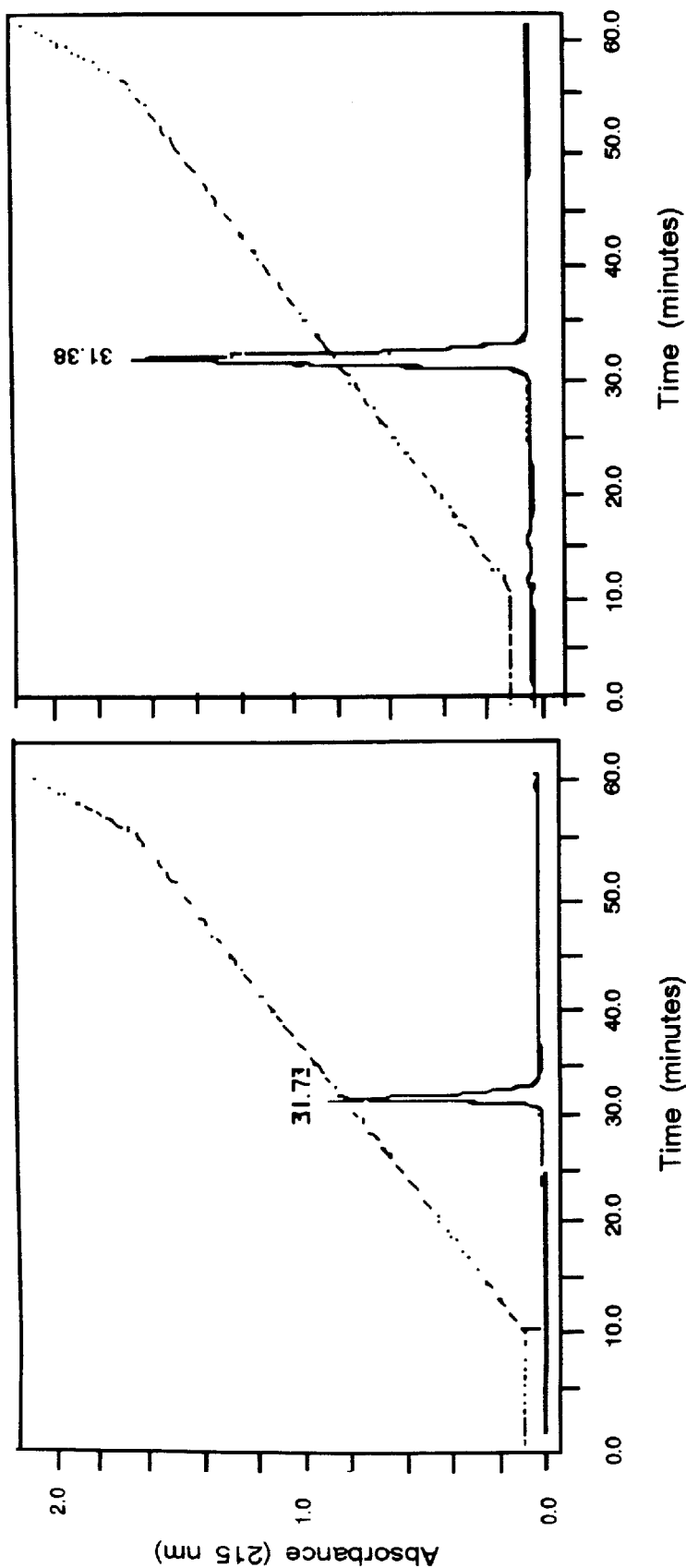
FIGS. 4(A)–FIG. 4(D) depict purification of CTLA-2β on reverse-phase chromatography, with: 4(A) showing elution profiles for monomeric and 4(B) showing dimeric species on a Vydac C4 reverse phase colum; and, showing the analysis for the monomer and dimer fractions monitored by SDS-PAGE.

The monomeric CTLA-2β from the superdex-75 column was subjected to Q-Sepharose chromatography. The CTLA-2β monomer eluted at 0.32M NaCl and was separated from the proteolytically cleaved monomer and most of the dimeric species (FIG. 3). Fractions 20–28 were pooled and found to be approximately 90% pure monomeric CTLA-2β. Fractions 29–34 were used as a source for the dimer. A portion of each of these pools were subjected to chromatography on a reverse-phase C4 column to obtain highly purified material for characterization studies (FIG. 4).

Monomer and dimer both eluted at 39% acetonitrile with the only contaminants being other CTLA-2β species, as determined by western analysis. The monomer sample was approximately 95% pure while the dimer sample was contaminated with both monomer and proteolytically modified monomer. All of the characterization studies listed below were carried out on the reverse phase purified material unless stated otherwise.

TABLE 2

AMINO ACID COMPOSITION

|     | PMOL    | HOI % | NORM  | KNOWN | DIFFERENCE | % DIFF |
|-----|---------|-------|-------|-------|------------|--------|
| Asp | 939.441 | 13.82 | 14.91 | 13    | 1.91       | 14.7   |
| Glu | 1067.08 | 15.70 | 16.94 | 16    | 0.94       | 5.9    |
| Ser | 503.311 | 7.41  | 7.99  | 8     | −0.01      | −0.1   |
| Gly | 424.619 | 6.25  | 6.74  | 6     | 0.74       | 12.3   |
| His | 130.202 | 1.92  | 2.07  | 2     | 0.07       | 3.3    |
| Arg | 458.503 | 6.75  | 7.28  | 7     | 0.28       | 4.0    |
| Thr | 380.579 | 5.60  | 6.04  | 6     | 0.04       | 0.7    |
| Ala | 496.92  | 7.31  | 7.89  | 8     | −0.11      | −1.4   |
| Pro | 501.314 | 7.38  | 7.96  | 8     | −0.04      | −0.5   |
| Tyr | 316.291 | 4.65  | 5.02  | 5     | 0.02       | 0.4    |
| Val | 21.089  | 0.31  | 0.33  |       | 0.33       | ERR    |
| Met | 225.013 | 3.31  | 3.57  | 5     | −1.43      | −28.6  |
| Cys | 0.00    | 0.00  | 0.00  | 0     | 0.00       | ERR    |
| Ile | 81.052  | 1.19  | 1.29  | 1     | 0.29       | 28.7   |
| Leu | 500.976 | 7.37  | 7.95  | 8     | −0.05      | −0.6   |
| Nlu | 980.718 |       |       |       |            | ERR    |
| Phe | 250.685 | 3.69  | 3.98  | 4     | −0.02      | −0.5   |
| Lys | 498.543 | 7.34  | 7.91  | 8     | −0.09      | −1.1   |
| Trp |         | 0.00  | 0.00  |       | 0.00       | ERR    |

Norm MW: 12327.6 Known MW: 12903.0 Accuracy: 95.2% Pmol Analyzed: 63.0 NG Analyzed: 813 Pmol Hydrolyzed: 240.8 NG Hydrolyzed: 3107

Amino Acid Analysis of 240.0 pmoles CTLA-2β monomer post C4 Reverse-Phase Chromatography.

C) Characterization of CTLA-2β.

(i) Amino Acid Analysis: 240 pmoles of CTLA-2β monomer from C-4 chromatography was hydrolyzed and the amino acid composition was determined. The composition had an accuracy of 95.2% when normalized to the known sequence of CTLA-2β (Table 2, above).

Figure 5:
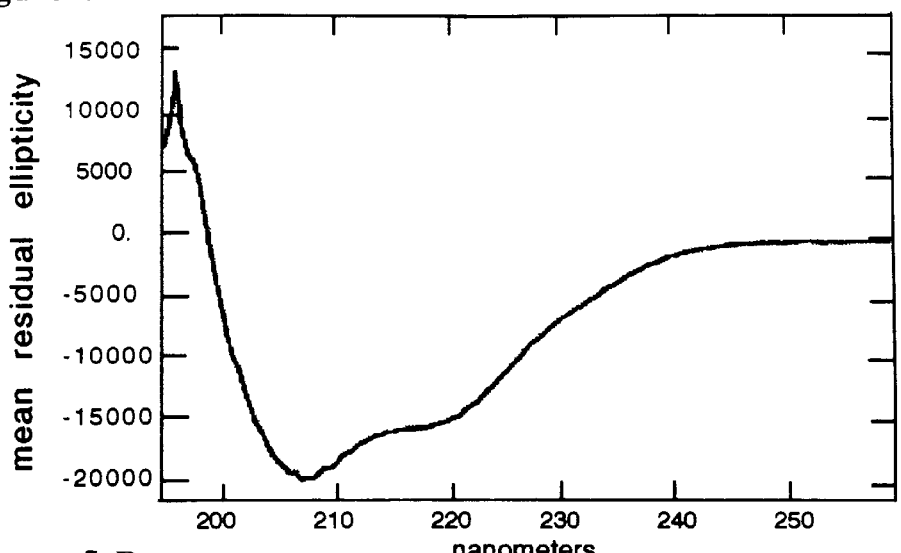
Figure 5:
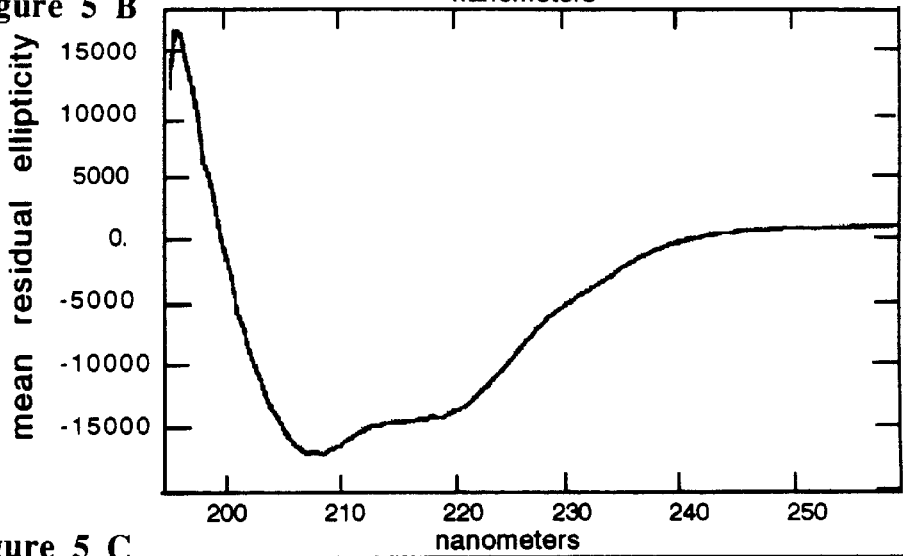
Figure 5:
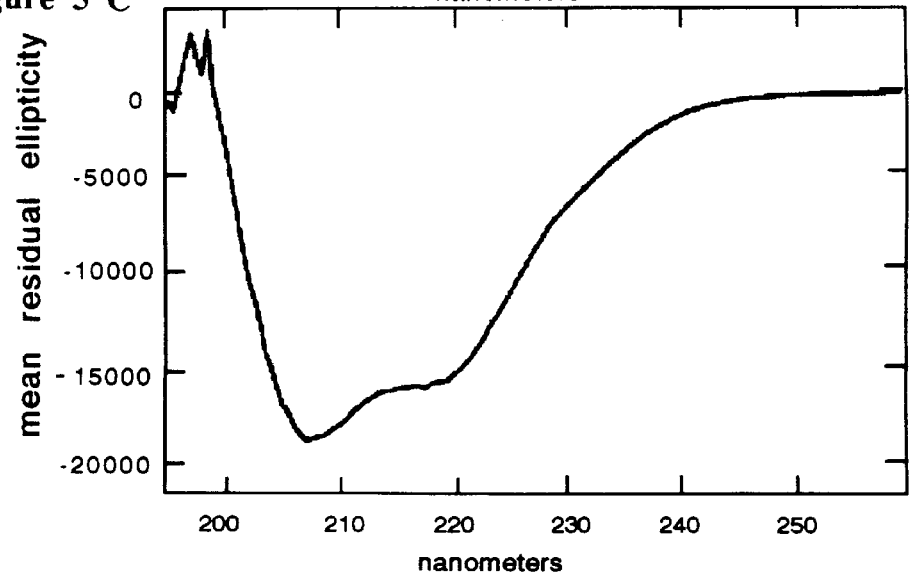

(ii) Circular Dichroism: The CD spectra of monomeric CTLA-2β post Q-Sepharose chromatography (0.226 mg/ml in PBS), monomeric CTLA-2β post C-4 chromatography (0.505 mg/ml in PBS) was taken from 195 to 300 nm, and the resulting spectra are shown in FIG. 5. No difference in the spectra of the monomeric species either before or after reverse-phase chromatography could be found; indicating that treatment with acetonitrile did not effect the secondary structure. However, as listed in Table 3 below, the monomer had 67% B structure while the dimer had 53%. The dimer also showed B turn, whereas the monomer did not. Therefore, it appears as if the protein does undergo some structural changes upon forming the covalent dimer.

(iii) Mass Spectrophotometry: The mass spectra of monomeric (0.226 mg/ml in PBS) and dimeric CTLA-2β (0.505 mg/ml in PBS) of CTLA-2β from step (iv) of Example 2 was analyzed using a Finigan LASERMAT Mass Spectrophotometer. The results are tabulated in Table 3, below. It was determined that the monomeric form of CTLA-2β has a mass of 12.8 kd, and the dimeric form a mass of 25.4 kd.

TABLE 3

CHARACTERIZATION OF CTLA-2β

|                          | MONOMER  | DIMER    |
|--------------------------|----------|----------|
| Molecular Weight:        |          |          |
| on Gel filtration        | 28 kd    | 56 kd    |
| from non-reducing gel    | 14 kd    | 28 kd    |
| from Mass Spec.          | 12.8 kd  | 25.4 kd  |
| Circular Dichroism:      |          |          |
| % Alpha Helix            | 7.6      | 8.6      |
| % β-turn                 | 0.0      | 10.9     |
| % Random Coil            | 20.8     | 27.3     |
| % β-sheet                | 67.4     | 53.1     |
| i.c. 50 in Cathepsin L Assay | 18.2 nM | 1.1 nM |
| i.c. 50 in Cathepsin H Assay | 69 nM   | NA     |
| i.c. 50 in Papain Assay  | 14 nM    | NA       |

Summary of the Characterization of monomeric and dimeric CTLA-2β. The molecular weights of the monomeric and dimeric forms of CTLA-2β were determined by the various methods stated. The secondary structure to CTLA-2β was measured using Circular Dichroism and analyzed by comparing the resulting spectra to standard structures.

Figure 6:
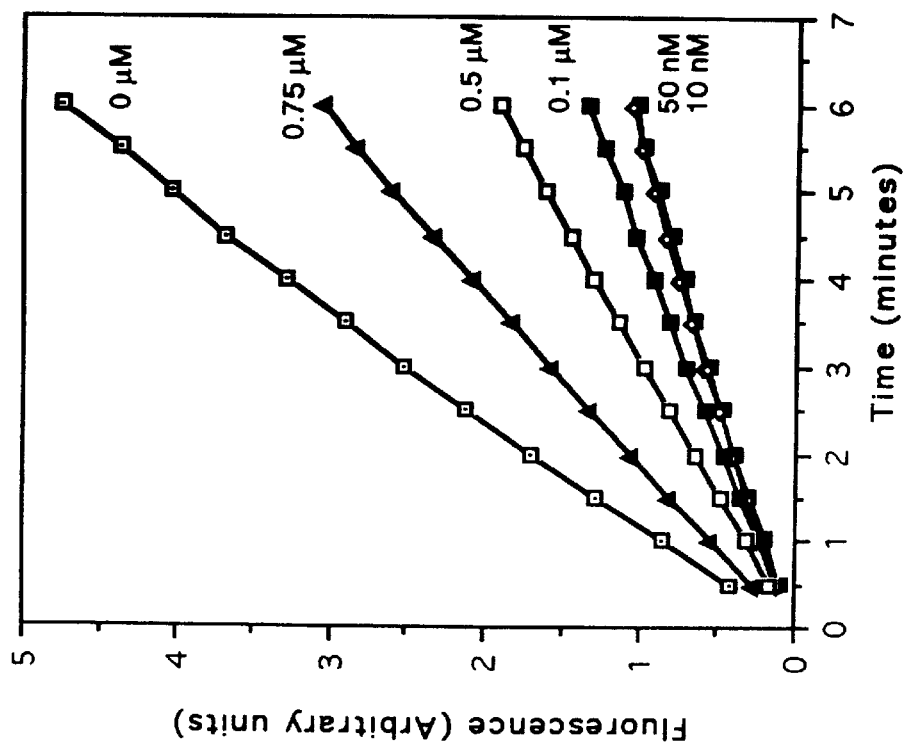
FIGS. 6(A)–6(D) graphically depict inhibition of Cathepsin L by CTLA-2β, the hydrolysis of Z-Phe-Arg-AMC by cathepsin L was measured by fluoresence at the concentration of monomer or dimer indicated: A plot of the fluoresence due to Cathepsin L activity vs. time for different concentrations of CTLA-2β, with data for both the monomer, FIG. 6(A), and the dimer, FIG. 6(B), shown, and also the crude fluorescence data as depicted in (A) and (B) analyzed on a Dixon plot of the form v−/v+ vs. CTLA-2β concentration are shown in 6(C) and 6(D).
Figure 6:
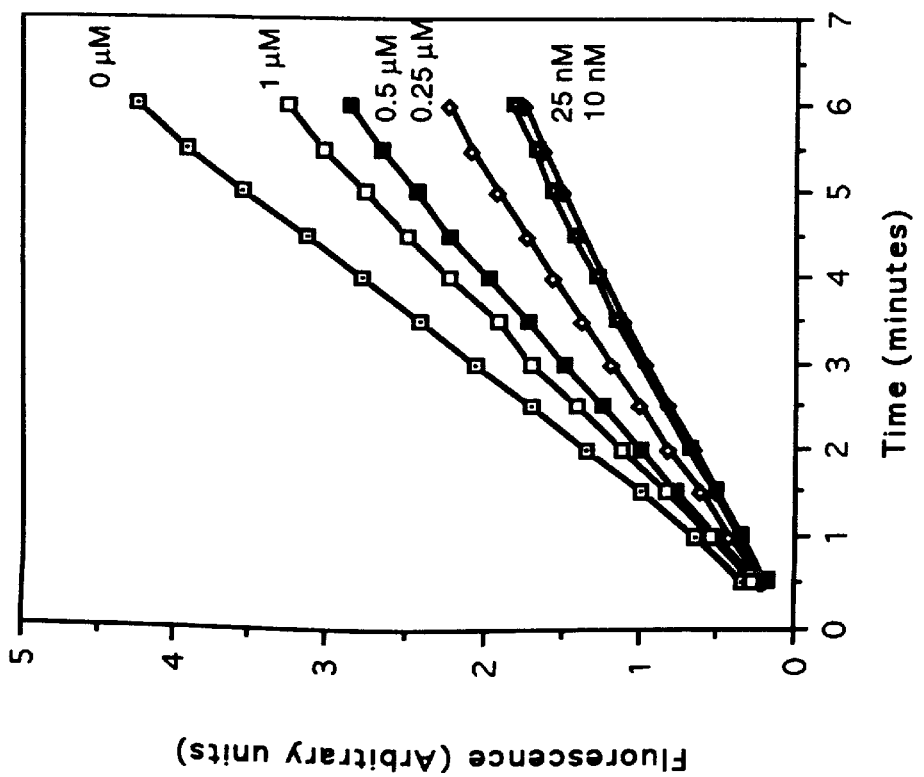
Figure 6:
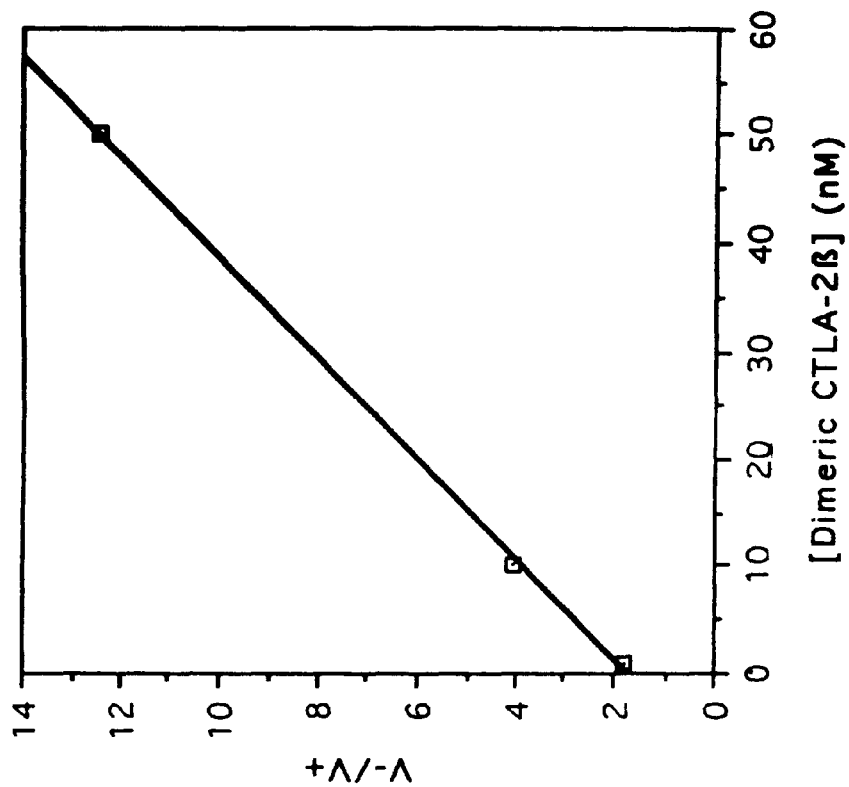
Figure 6:
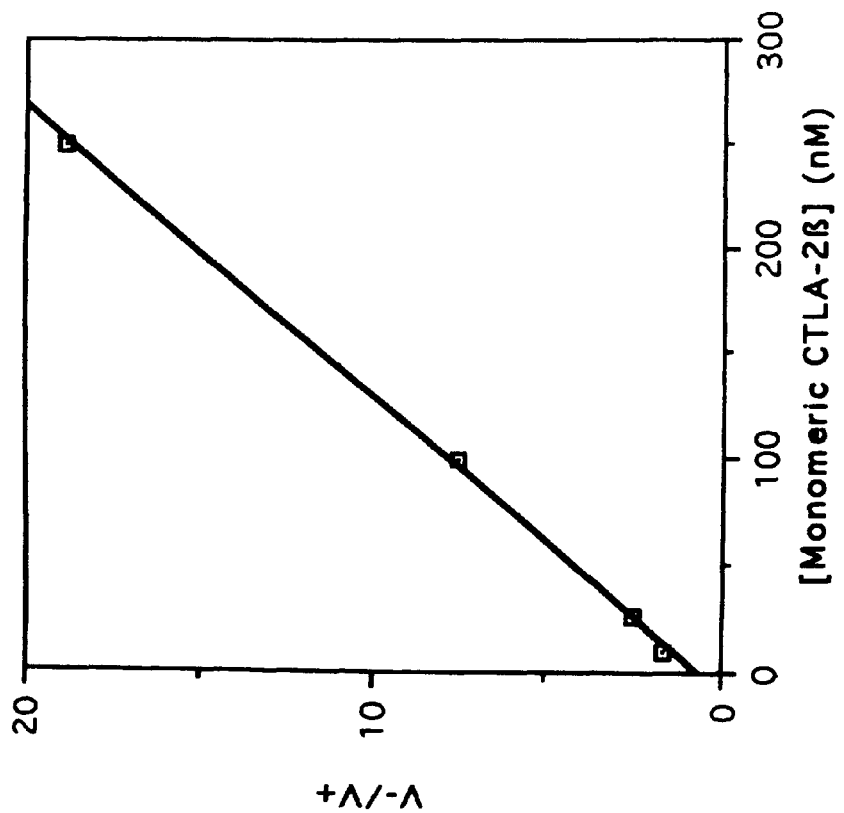

(iv) Inhibition of Cathepsin L: The synthetic substrate Z-Phe-Arg-NMec (AMC), was hydrolyzed by Cathepsin L to yield the intensely fluorescent 7-amino-4-methylcoumarin. Both monomeric and dimeric forms of CTLA-2β (from reverse-phase chromatography) were shown to have some inhibitory activity (FIGS. 6A and 6B).

Figure 7:
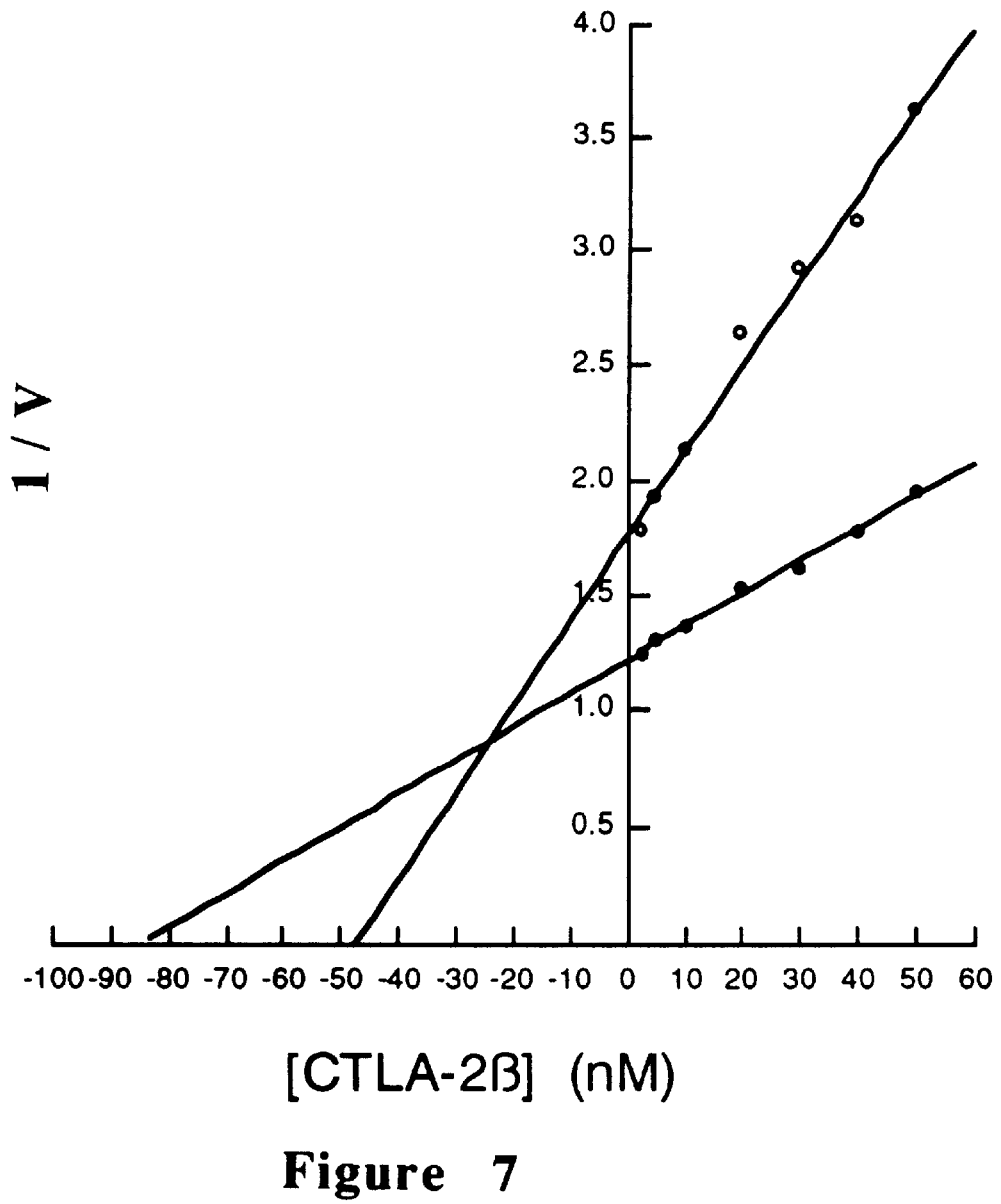
FIG. 7 shows the determination of the Ki value for the interaction of CTLA-2β with Cathepsin L using a Dixon plot of the form 1/V vs. CTLA-2β concentration. The concentration of Z-Phe-Arg-AMC used was 5 uM (closed circles) and 2.5 uM (open circles). Linear regression was performed to determine the Ki.

One characteristic observation is that CTLA-2β did not give 100% inhibition of the proteolytic activity of Cathepsin L even at high concentrations. The maximum inhibition observed was approximately 60%. This is different from other known inhibitors of Cathepsin L, such as the cystatins, that will completely inhibit the activity of the enzyme. However, from our data, an i.c. 50 value of 18 nM and 1.1 nM were observed for the inhibition of human liver Cathepsin L by monomeric and dimeric CTLA-2β, respectively (Table 3, above). A Ki value of 22 nM was obtained for the inhibition of human Cathepsin L with CTLA-2β indicating a tight interaction between these two proteins (FIG. 7).

In order to determine the specificity of CTLA-2β with respect to it's inhibition of various cysteine proteases, assays were set up for papain as well as Cathepsins H and L (see Example 4, above). The Dixon plot of the form V−/V+ vs. I for the inhibition of these proteases by CTLA-2β is shown in FIG. 8. From this plot, the i.c. 50 value has been calculated to be 14 nM for papain and 69 nM for Cathepsin H. It is interesting to note that CTLA-2β was able to inhibit 100% of the activity of papain compared to approximately 60% of the activity of Cathepsin L.

The above data leads to methods of making specific inhibitors of a given cathepsin. Through recombinant DNA techniques, a molecule can be constructed so that it is highly homologous to the pro-region of the protease yet retains the functional aspects of the CTLA-2β molecule.

EXAMPLE 5

Synthetic Peptides Derived from CTLA Inhibit Cathepsin L Activity

In an effort to further characterize the inhibitory regions of CTLA, and the protease inhibiting activity as demonstrated by the previous examples, four synthetic peptides were generated based on the peptide sequence for CTLA.

p117: YSLDQQRHRRLMWEENKKKIEAH [SEQ ID No. 5]

p118: SLDNEWKEWKTTFAKAYSLDEE [SEQ ID No. 6]
p089: ENKKKIEAHNADYERGKTSFC [SEQ ID No. 7]
p092: CRGEMAPDLPEYEDLG [SEQ ID No. 8]

The peptides were synthesized on a model 430A (Applied Biosystems) peptide synthesizer using NMP-HOBt Fmoc chemistry. The peptides were cleaved and deprotected in 90% TFA, 4% thioanisole, 2% ethanedithiol, and 4% liquefied phenol for 2 hours at room temperature. After lyophilization, the peptides were purified by C18 reverse-phase chromatography on a Beckman System Gold HPLC.

These peptides were tested for inhibition of Cathepsin L activity using the assays described previously. Briefly, Cathepsin L (19 pM final as determined by active site titration using E-64, Barret & Kirschke, 1991) was added to 750 uL of assay buffer consisting of 340 nM sodium acetate—60 mM acetic acid (pH 5.5), 4 mM disodium EDTA, and 8 mM DTT. Peptides were added at concentrations ranging from on to 35 uM. After a 6 minute incubation at 25° C., 1500 uL of 0.1% Brij 35 was added and the reaction started with 5.0 uM Z-Phe-Arg-NMec(AMC) (AMC is aminomethylcoumarin). The fluorescence of the free aminomethylcoumarin was measured in an SLM 4800s fluorimeter at excitation of 370 nm and an emission at 432 nm over a 6 minute time period. Fluorescence was converted to uM AMC released by using a standard curve generated by plotting uM AMC vs. fluorescence, and plotted vs. time. In order to calculate the velocities, a linear least squares analysis was performed over the initial part of the data. Correlation coefficients were greater than 0.98 in all cases. The i.c. 50 values were determined from Dixon plots of the form V-/V+ (velocity without peptide/velocity with peptide) vs. peptide concentration. From these tests, the following results were obtained.

TABLE 4

I.C. 50 DETERMINATION

| Peptide | i.c. 50 |
|---------|---------|
| p117 | 5.3 uM |
| p092 | 41 uM |
| p089 | 10 uM inhibited 25% |
| p118 | no inhibition at 1000 uM |

FIG. 9A is a graph of the data for the assays using the p117 peptide, [SEQ ID No. 5]. FIG. 9B is a Dixon plot derived from this data. The various symbols plot different concentrations of peptide tested (in uM).

FIG. 10A is a graph of the data for the assays using the p092 peptide, [SEQ ID No. 8]. FIG. 10B is a Dixon plot derived from this data. The various symbols plot different concentrations of peptide tested (in uM) as labelled.

FIG. 11A is a graph of the data for the assays using the p089, [SEQ ID No. 7] peptide. FIG. 11B is a graph of the data for the assays using the p118 peptide, [SEQ ID No. 6]. The various symbols plot different concentrations of peptide tested (in uM) as labeled.

From these data it can be seen that the synthetic polypeptide p117 is capable of effecting the inhibition of cysteine protease activity in vitro. The results also indicate varying effectiveness of other synthetic peptides under similar assay conditions. Thus the p117 peptide is a useful agent for inhibiting cysteine protease activity.

EXAMPLE 6

Synthetic Peptides Derived from CTLA Inhibit Proteoglycan Degradation

Cathepsins B and L have been found to degrade cartilage components, causing the degradation of associated proteoglycans. (Maciewicz and Wotton, 1991, Biomed. Biochim. Acta 50:561). Previous results by the same researchers indicated that these enzymes are found in active form in the synovial fluid of arthritic patients. The conclusion drawn was that cysteine proteinases play a role in the etiology of arthritis.

Cartilage degradation can be induced by the in vivo injection of IL-1 into the joint capsule of rabbits, and the administration of a large serine protease inhibitor PN-1 (43 KD) can ameliorate this degradation. It has been found that low molecular weight synthetic peptide metalloproteinase inhibitor can prevent the breakdown of proteoglycan within articular cartilage in vitro. (Andrews et al., 1992, Agents Actions 37:147). Certain cysteine endopeptidase inactivators were found to inhibit IL-1 stimulated structural cartilage proteoglycan degradation. E64 and Ep475, broad-spectrum cysteine protease inhibitors) did not work at 100 uM concentrations. However lipophillic derivatives inhibited at 10 uM to 1 uM concentrations. (Buttle et al., 1992, Arch Biochem Biophys 299:377). The peptides described in the previous example were thus tested for the ability to inhibit articular cartilage proteoglycan degradation, as measured by proteoglycan release after IL-1 stimulation.

The assay system used for testing the peptides for inhibitory activity of proteoglycan release is a micro organ culture assay (MOCA). Papain; cetyl pyridinium chloride and chondroitin sulfate type C was purchased from Sigma Chemical Co. (St. Louis, Mo.). Interleukin 1 alpha was purchased from Collaborative Research. ABCase, chrondroitinase, ABC lyase, and keratanase were obtained from ICI. Na $^{35}SO_4$ was purchased from NEN.

Articular cartilage explants from calf knee joints were maintained in culture in DMEM medium containing 20 uCi/ml Na $^{35}SO_4$ for 48 hours for the incorporation of label into newly synthesized proteoglycan (PG). The radiolabelled medium was then removed, the radiolabelled explants washed 3×30 ml cold DMEM and placed into a 96 well plate with or without IL-1 (Interleukin-1 alpha, 50 U/ml) and various concentrations of p117. The explants were incubated first for 24 hours in the presence of IL-1 in order to ensure initiation of IL-1 induced auto-catalysis prior to the addition of various metalloprotease inhibitors for an additional 72 hours.

The newly synthesized radiolabelled proteoglycans released during the cultivation period were subjected to enzymatic digestion with papain. Briefly, an aliquot of 150 ul of medium from the original culture volume (300 ul) was incubated with 100 ul of papain (3 mg/ml) for 2 hours at 65° C. A 50 ul aliquot of the papain digested material containing radiolabelled $^{35}SO_4$-gag (glycosaminoglycans, mucopolysaccharide) was incubated with 100 ul of cetylpyridinium chloride (cpc, 4% cpc+40 nM $NaSO_4$) plus cold chondroitin sulfate standard (30 ul of 2.5 mg/ml solution). The samples were placed on ice for 60 minutes, and the radiolabelled gags were precipitated and collected on a 96 well plate harvester (MACH2, TOMTEC, Orange, CT) glass fiber filter. The filter was dried and counted after addition of 10 mls of scintillation cocktail (scintillant).

FIG. 12 is a graph showing inhibition of proteoglycan release from MOCA by p117 peptide. The ability of p117 to inhibit the IL-1 induced degradation of articular cartilage was shown to be best at a concentration of p117 of 10 uM. The resulting inhibition is about 30%.

These results indicate that the synthetic peptide p117, acting on the activity of Cathepsin L and/or Cathepsin B is effective as an inhibitor of proteoglycan release in situ. The MOPC assay is an acceptable model system for in vivo disease of the connective tissues, and indicate that the p117 polypeptide would be an effective agent for use in vivo.

EXAMPLE 7

Theoretical Minimum Inhibitory Polypeptide

Conserved Sequence

Examination of the human Cathepsin L proregion sequence (SEQ ID NO. 12) and the mouse Cathepsin L proregion sequence (SEQ ID NO. 13) reveals regions of homolgy. This combined with the findings of the activity of the peptides of the present invention lead to the conclusion that there could be a minimum conserved sequence that will maintain inhibitory activity.

Taking into account that the best activity was found for p117, (residues 26–47), the partial activity of p089 (residues 39–58), and the poor activity of p118 (residues 9–30), the comparison narrowed down the ideal conserved sequence as set out in the table below.

Human CATL TLTFDHSLEAQWTKW KAMHNRLYGM-NEEGW RRAVWEKNMKMIELH N
Mouse CATL DQTF--S--AEWHQW KSTHRRLYGT-NEEEW RRAIWEKNMRMIQLH N
CTLA B ----DPSLDNEWKEW KTTFAKAYSLDEERH RRLMWEENKKKIEAH N huCATL QEYREGKHSFTMAM NAFGDMTSEEFRQVM NGFQNRKPRKGKVFQ EPLFYE muCATL GEYSNGQHGFSMEM NAFGDMTNEE-FRQVV NGYRHQKHKKGRLFQ EPLMLK CTLA B ADYERGKTSFYMGL NQFSDLTPEEFRTNC CGSSMCRGEMAPDLP EYEDLG
CTLA B KNSYLTPGRAQPE The high-lighted segment corresponds to what is believed to be the minimal conserved inhibition sequence. We would predict that these peptide fragments will act as effective inhibitory peptides.

Human CATL RRAVWEKNMKMIELHN (SEQ ID NO. 9)
Mouse CATL RRAIWEKNMRMIQLHN (SEQ ID NO. 10)
CTLA B RRLMWEENKKKIEAHN (SEQ ID NO. 11)

The advantage of using the peptide sequence that is based upon the human sequence is that it may be more specific, and perhaps lack antigenicity in human patients.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as the invention, the following claims conclude this specification.

What we claim:

1. A polypeptide having an amino acid sequence selected from the group consisting of the amino acid sequence of SEQ ID NO:5 (p117), SEQ ID NO:6 (p118), SEQ ID NO:7 (p089), and SEQ ID NO:8 (p092).

2. A polypeptide having an amino acid sequence selected from the group consisting of the amino acid sequence of SEQ ID NO:9 (huCATL homolog), SEQ ID NO:10 (muCATL homolog), and SEQ ID NO:11 (CTLA B homolog).

3. A polypeptide dimer, wherein at least one polypeptide dimer component is a polypeptide having the amino acid sequence of SEQ ID NO:4, and the second polypeptide dimer component is a polypeptide of claim 1.

4. A polypeptide dimer of claim 3, wherein said dimer has an apparent molecular weight of between 22 and 28 kDa as measured by SDS PAGE.

5. A method for inhibiting the proteolytic activity of a cysteine protease in vitro comprising contacting said cysteine protease with an effective inhibiting amount of at least one polypeptide which has an amino acid sequence selected from the group consisting of the amino acid sequence of SEQ ID NO:5 (p117), SEQ ID NO:7 (p089), SEQ ID NO:8 (p092), SEQ ID NO:11 (CTLA B homolog), SEQ ID NO:9 (huCATL homolog), and SEQ ID NO:10 (muCATL homolog).

6. The method of claim 5, wherein the cysteine protease is selected from the group consisting of Cathepsin H, Cathepsin L, and papain.

7. A method for inhibiting the degradation of proteoglycans in vitro comprising administering an effective inhibiting amount of at least one polypeptide which has the amino acid sequence selected from the group consisting of the amino acid sequence of SEQ ID NO:5 (p117), SEQ ID NO:7 (p089), SEQ ID NO:8 (p092), SEQ ID NO:11 (CTLA B homolog), SEQ ID NO:9 (huCATL homolog), and SEQ ID NO:10 (muCATL homolog).

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 141 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..141
        (D) OTHER INFORMATION: /note= "clta-2b from Denizot et
            al., Eur. J. Immunol. 19:631-635 (1989)"

(xi) SEQUENCE DESCRIPTION: SEQ ID NO:1:

Leu Asp Asn Lys Val Leu Val Ser Ile Cys Glu Gln Lys Leu Gln His
1               5                   10                  15

Phe Ser Ala Val Phe Leu Leu Ile Leu Cys Leu Gly Met Met Ser Ala
                20                  25                  30

Ala Pro Ser Pro Asp Pro Ser Leu Asp Asn Glu Trp Lys Glu Trp Lys
            35                  40                  45

Thr Thr Phe Ala Lys Ala Tyr Ser Leu Asp Glu Glu Arg His Arg Arg
        50                  55                  60

Leu Met Trp Glu Glu Asn Lys Lys Lys Ile Glu Ala His Asn Ala Asp
65                  70                  75                  80

```
Tyr Glu Arg Gly Lys Thr Ser Phe Tyr Met Gly Glu Asn Gln Phe Ser
             85                  90                  95

Asp Leu Thr Pro Glu Glu Phe Arg Thr Asn Cys Cys Gly Ser Ser Met
            100                 105                 110

Cys Arg Gly Glu Met Ala Pro Asp Leu Pro Glu Tyr Glu Asp Leu Gly
            115                 120                 125

Lys Asn Ser Tyr Leu Thr Pro Gly Arg Ala Gln Pro Glu
            130                 135                 140
```

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "5' primer for ctla-2b"

(xi) SEQUENCE DESCRIPTION: SEQ ID NO:2:

GGGGGATCCA TGGCTGCTCC ATCC                                      24

(2) INFORMATION FOR SEQ ID NO:3:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "3' primer for clta-2b"

(xi) SEQUENCE DESCRIPTION: SEQ ID NO:3:

TGTGGACCTT CCCGAGTCGG TCTCATTCGA TCGCCTAGGG GG                  42

(2) INFORMATION FOR SEQ ID NO:4:

(i) SEQUENCE CHARACTERISTICS:
        (A) LENGTH: 111 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:4:

```
Met Ala Ala Pro Ser Pro Asp Pro Ser Leu Asp Asn Glu Trp Lys Glu
1               5                  10                  15

Trp Lys Thr Thr Phe Ala Lys Ala Tyr Ser Leu Asp Glu Glu Arg His
             20                  25                  30

Arg Arg Leu Met Trp Glu Glu Asn Lys Lys Lys Ile Glu Ala His Asn
             35                  40                  45

Ala Asp Tyr Glu Arg Gly Lys Thr Ser Phe Tyr Met Gly Leu Asn Gln
             50                  55                  60

Phe Ser Asp Leu Thr Pro Glu Glu Phe Arg Thr Asn Cys Cys Gly Ser
65                  70                  75                  80

Ser Met Cys Arg Gly Glu Met Ala Pro Asp Leu Pro Glu Tyr Glu Asp
                 85                  90                  95

Leu Gly Lys Asn Ser Tyr Leu Thr Pro Gly Arg Ala Gln Pro Glu
                100                 105                 110
```

(2) INFORMATION FOR SEQ ID NO:5:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..23
        (D) OTHER INFORMATION: /note= "p117 SYNTHETIC PEPTIDE"

(xi) SEQUENCE DESCRIPTION: SEQ ID NO:5:

```
Tyr Ser Leu Asp Glu Glu Arg His Arg Arg Leu Met Trp Glu Asn
1               5                   10                  15

Lys Lys Lys Ile Glu Ala His
            20
```

(2) INFORMATION FOR SEQ ID NO:6:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..22
        (D) OTHER INFORMATION: /note= "p118 SYNTHETIC PEPTIDE"

(xi) SEQUENCE DESCRIPTION: SEQ ID NO:6:

```
Ser Leu Asp Asn Glu Trp Lys Glu Trp Lys Thr Thr Phe Ala Lys Ala
1               5                   10                  15

Tyr Ser Leu Asp Glu Glu
            20
```

(2) INFORMATION FOR SEQ ID NO:7:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..21
        (D) OTHER INFORMATION: /note= "p089 SYNTHETIC PEPTIDE"

(xi) SEQUENCE DESCRIPTION: SEQ ID NO:7:

```
Glu Asn Lys Lys Lys Ile Glu Ala His Asn Ala Asp Tyr Glu Arg Gly
1               5                   10                  15

Lys Thr Ser Phe Cys
            20
```

(2) INFORMATION FOR SEQ ID NO:8:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: Not Relevant (ii) MOLECULE TYPE: peptide (ix) FEATURE:
              (A) NAME/KEY: Peptide
              (B) LOCATION: 1..16
              (D) OTHER INFORMATION: /note= "p092 SYNTHETIC PEPTIDE"

(xi) SEQUENCE DESCRIPTION: SEQ ID NO:8:

Cys Arg Gly Glu Met Ala Pro Asp Leu Pro Glu Tyr Glu Asp Leu Gly
1               5                   10                  15

(2) INFORMATION FOR SEQ ID NO:9:

(i) SEQUENCE CHARACTERISTICS:
              (A) LENGTH: 16 amino acids
              (B) TYPE: amino acid
              (C) STRANDEDNESS: Not Relevant
              (D) TOPOLOGY: Not Relevant (ii) MOLECULE TYPE: peptide (xi) SEQUENCE DESCRIPTION: SEQ ID NO:9:

Arg Arg Ala Val Trp Glu Lys Asn Met Lys Met Ile Glu Leu His Asn
1               5                   10                  15

(2) INFORMATION FOR SEQ ID NO:10:

(i) SEQUENCE CHARACTERISTICS:
              (A) LENGTH: 16 amino acids
              (B) TYPE: amino acid
              (C) STRANDEDNESS: Not Relevant
              (D) TOPOLOGY: Not Relevant (ii) MOLECULE TYPE: peptide (xi) SEQUENCE DESCRIPTION: SEQ ID NO:10:

Arg Arg Ala Ile Trp Glu Lys Asn Met Arg Met Ile Gln Leu His Asn
1               5                   10                  15

(2) INFORMATION FOR SEQ ID NO:11:

(i) SEQUENCE CHARACTERISTICS:
              (A) LENGTH: 16 amino acids
              (B) TYPE: amino acid
              (C) STRANDEDNESS: Not Relevant
              (D) TOPOLOGY: Not Relevant (ii) MOLECULE TYPE: peptide (xi) SEQUENCE DESCRIPTION: SEQ ID NO:11:

Arg Arg Leu Met Trp Glu Glu Asn Lys Lys Ile Glu Ala His Asn
1               5                   10                  15

(2) INFORMATION FOR SEQ ID NO:12:

(i) SEQUENCE CHARACTERISTICS:
              (A) LENGTH: 96 amino acids
              (B) TYPE: amino acid
              (C) STRANDEDNESS: Not Relevant
              (D) TOPOLOGY: Not Relevant (ii) MOLECULE TYPE: protein (ix) FEATURE:
              (A) NAME/KEY: Protein
              (B) LOCATION: 1..96
              (D) OTHER INFORMATION: /note= "huCATL"

(xi) SEQUENCE DESCRIPTION: SEQ ID NO:12:

Thr Leu Thr Phe Asp His Ser Leu Glu Ala Gln Trp Thr Lys Trp Lys
1               5                   10                  15

```
Ala Met His Asn Arg Leu Tyr Gly Met Asn Glu Glu Gly Trp Arg Arg
            20                  25                  30

Ala Val Trp Gly Lys Asn Met Lys Met Ile Glu Leu His Asn Gln Glu
            35                  40                  45

Tyr Arg Glu Gly Lys His Ser Phe Thr Met Ala Met Asn Ala Phe Gly
 50                      55                  60

Asp Met Thr Ser Glu Glu Phe Arg Gln Val Met Asn Gly Phe Gln Asn
65                   70                  75                  80

Arg Lys Pro Arg Lys Gly Lys Val Phe Gln Gln Pro Leu Phe Tyr Glu
                85                  90                  95

(2) INFORMATION FOR SEQ ID NO:13:

(i) SEQUENCE CHARACTERISTICS:
        (A) LENGTH: 92 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..92
        (D) OTHER INFORMATION: /note= "muCATL"

(xi) SEQUENCE DESCRIPTION: SEQ ID NO:13:

Asp Gln Thr Phe Ser Ala Glu Trp His Gln Trp Lys Ser Thr His Arg
1                5                  10                  15

Arg Leu Tyr Gly Thr Asn Glu Glu Glu Trp Arg Arg Ala Ile Trp Glu
            20                  25                  30

Lys Asn Met Arg Met Ile Gln Leu His Asn Gly Glu Tyr Ser Asn Gly
            35                  40                  45

Gln His Gly Phe Ser Met Glu Met Asn Ala Phe Gly Asp Met Thr Asn
        50                  55                  60

Glu Glu Phe Arg Gln Val Val Asn Gly Tyr Arg His Gln Lys His Lys
65                  70                  75                  80

Lys Gly Arg Leu Phe Gln Gln Pro Leu Met Leu Lys
                85                  90
```